United States Patent [19]
Doll et al.

[11] Patent Number: 5,891,872
[45] Date of Patent: Apr. 6, 1999

[54] TRICYCLIC COMPOUNDS

[75] Inventors: Ronald J. Doll, Maplewood; Alan K. Mallams, Hackettstown; Adriano Afonso, West Caldwell; Dinanath F. Rane, Morganville; F. George Njoroge, Union; Randall R. Rossman, Nutley, all of N.J.

[73] Assignee: Schering Corporation, Kenilworth, N.J.

[21] Appl. No.: 446,980

[22] Filed: May 22, 1995

Related U.S. Application Data

[63] Continuation of Ser. No. 418,982, Apr. 7, 1995, abandoned.
[51] Int. Cl.$^6$ .......................... A61K 31/55; C07D 403/06
[52] U.S. Cl. .............................. 514/220; 540/495
[58] Field of Search .............................. 540/495; 514/220

[56] References Cited

U.S. PATENT DOCUMENTS

| | | | |
|---|---|---|---|
| 4,282,233 | 8/1981 | Villani | 546/93 |
| 4,826,853 | 5/1989 | Piwinski et al. | 514/290 |
| 4,831,042 | 5/1989 | Villani | 514/316 |
| 4,863,931 | 9/1989 | Schumacher et al. | 514/290 |
| 5,089,496 | 2/1992 | Piwinski et al. | 514/253 |
| 5,104,876 | 4/1992 | Piwinski et al. | 514/254 |
| 5,141,851 | 8/1992 | Brown et al. | 435/15 |
| 5,151,423 | 9/1992 | Piwinski et al. | 514/254 |

FOREIGN PATENT DOCUMENTS

| | | |
|---|---|---|
| 0042544 | 12/1981 | European Pat. Off. |
| 0270818 | 6/1988 | European Pat. Off. |
| 0396083 | 11/1990 | European Pat. Off. |
| 0495484 | 7/1992 | European Pat. Off. |
| 0535730 | 4/1993 | European Pat. Off. |
| WO88/03138 | 5/1988 | WIPO |
| WO89/10363 | 11/1989 | WIPO |
| WO90/13548 | 11/1990 | WIPO |
| WO92/00293 | 1/1992 | WIPO |
| WO92/11034 | 7/1992 | WIPO |
| WO94/04561 | 3/1994 | WIPO |
| WO94/24107 | 10/1994 | WIPO |
| WO95/00497 | 1/1995 | WIPO |

OTHER PUBLICATIONS

*Cell*, 65, 1–4 (1991).
*J. Biol. Chem.*, 266, (24) 15575–15578 (1991).
*Proc. Natl. Acad. Sci. USA*, 87, 3042–3046 (1990).
*Proc. Natl. Acad. Sci. USA*, 88, 8631–8635 (1991).
*Nature*, 356, 713–715 (1992).
*Proc. Natl. Acad. Sci. USA*, 87, 7541–7545 (1990).
*J. Biol. Chem.*, 265, (25) 14701–14704 (1990).
*Proc. Natl. Acad. Sci. USA*, 87, 7926–7929 (1990).
*Cell*, 62, 81–88 (1990).
*Biochemistry*, 31, 3800–3807. (1992).
*Science*, 260, 1934–1937. Kohl et al 25 Jun. 1993.
*Science*, 260, 1937–1942. James et al. 25 Jun. 1993.
Piwinski, et al., *J. Med. Chem.*, 34, (1) 457–461 (1991).
Chem Abstracts No. 121:53129x (1994) for WO94/04561.
Masci, *J. Chem. Soc., Chem. Commun.*, 1262–1263 (1982).
Masci, *J. Org. Chem.*, 50, 4081–4087 (1985).
Sebti, et al., *Proc. Ann. Meeting AM Assoc. Cancer Res.*, 33:A2217 (19920.
Villani, et al., *J. Med. Chem.*, 15, (7) 750–754 (1972).
Billah, et al., *Lipids*, 26, (12) 1172–1174 (1991).
Villani, et al., *Arzneim.–Forsch./Drug Res.*, 36(II), 1311–1314 (1986).

*Primary Examiner*—Richard L. Raymond
*Attorney, Agent, or Firm*—Henry C. Jeanette

[57] ABSTRACT

Novel compounds of Formula

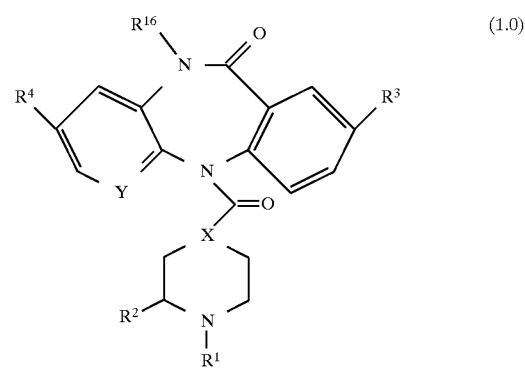

(1.0)

are disclosed. Also disclosed is a method of inhibiting Ras function and therefore inhibiting the abnormal growth of cells. The method comprises administering a compound of the formula to a biological system. In particular, the method inhibits the abnormal growth of cells in a mammal such as a human being.

17 Claims, No Drawings

TRICYCLIC COMPOUNDS

This is a continuation of application Ser. No. 08/418,982, filed Apr. 7, 1995, now abandoned.

BACKGROUND

International Publication Number WO92/11034, published Jul. 9, 1992, discloses a method of increasing the sensitivity of a tumor to an antineoplastic agent, which tumor is resistant to the antineoplastic agent, by the concurrent administration of the antineoplastic agent and a potentiating agent of the formula:

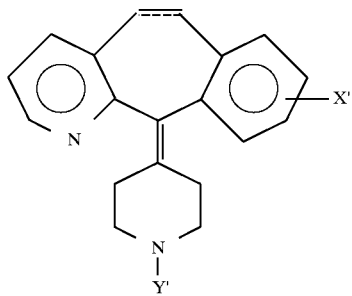

wherein the dotted line represents an optional double bond, X' is hydrogen or halo, and Y' is hydrogen, substituted carboxylate or substituted sulfonyl. For example, Y' can be, amongst others, —COOR' wherein R' is C1 to C6 alkyl or substituted alkyl, phenyl, substituted phenyl, C7 to C12 aralkyl or substituted aralkyl or -2, -3, or -4 piperidyl or N-substituted piperidyl. Y' can also be, amongst others, SO$_2$R' wherein R' is C1 to C6 alkyl, phenyl, substituted phenyl, C7 to C12 aralkyl or substituted aralkyl. Examples of such potentiating agents include 11-(4-piperidylidene)-5H-benzo[5,6]cyclohepta[1,2-b]pyridines such as Loratadine.

Oncogenes frequently encode protein components of signal transduction pathways which lead to stimulation of cell growth and mitogenesis. Oncogene expression in cultured cells leads to cellular transformation, characterized by the ability of cells to grow in soft agar and the growth of cells as dense foci lacking the contact inhibition exhibited by non-transformed cells. Mutation and/or overexpression of certain oncogenes is frequently associated with human cancer.

To acquire transforming potential, the precursor of the Ras oncoprotein must undergo farnesylation of the cysteine residue located in a carboxyl-terminal tetrapeptide. Inhibitors of the enzyme that catalyzes this modification, farnesyl protein transferase, have therefore been suggested as anti-cancer agents for tumors in which Ras contributes to transformation. Mutated, oncogenic forms of ras are frequently found in many human cancers, most notably in more than 50% of colon and pancreatic carcinomas (Kohl et al., Science, Vol. 260, 1834 to 1837, 1993).

In view of the current interest in inhibitors of farnesyl protein transferase, a welcome contribution to the art would be compounds useful for the inhibition of farnesyl protein transferase. Such a contribution is provided by this invention.

SUMMARY OF THE INVENTION

Inhibition of farnesyl protein transferase by tricyclic compounds of this invention has not been reported previously. Thus, this invention provides a method for inhibiting farnesyl protein transferase using tricyclic compounds of this invention which: (i) potently inhibit farnesyl protein transferase, but not geranylgeranyl protein transferase I, in vitro; (ii) block the phenotypic change induced by a form of transforming Ras which is a farnesyl acceptor but not by a form of transforming Ras engineered to be a geranylgeranyl acceptor; (iii) block intracellular processing of Ras which is a farnesyl acceptor but not of Ras engineered to be a geranylgeranyl acceptor; and (iv) block abnormal cell growth in culture induced by transforming Ras.

This invention provides a method for inhibiting the abnormal growth of cells, including transformed cells, by administering an effective amount of a compound of this invention. Abnormal growth of cells refers to cell growth independent of normal regulatory mechanisms (e.g., loss of contact inhibition).

This includes the abnormal growth of: (1) tumor cells (tumors) expressing an activated Ras oncogene; (2) tumor cells in which the Ras protein is activated as a result of oncogenic mutation in another gene; and (3) benign and malignant cells of other proliferative diseases in which aberrant Ras activation occurs.

The compounds useful in the claimed methods are novel compounds represented by Formula 1.0

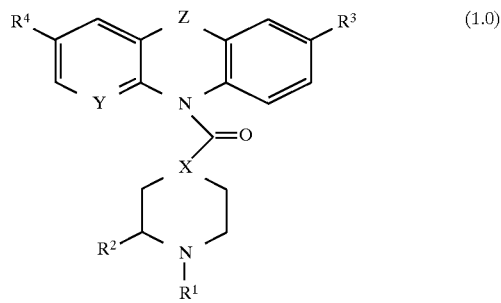

or a pharmaceutically acceptable salt or solvate thereof, wherein:

(1) $R^1$ is a group selected from:

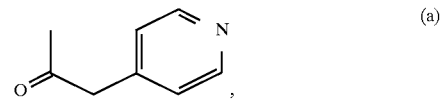

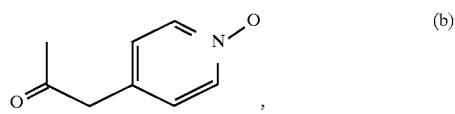

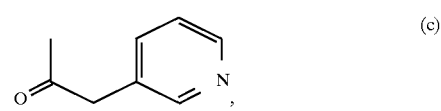

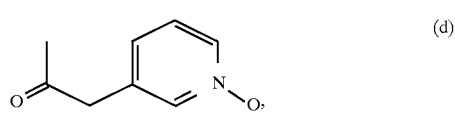

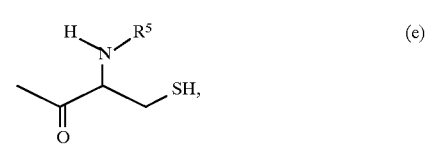

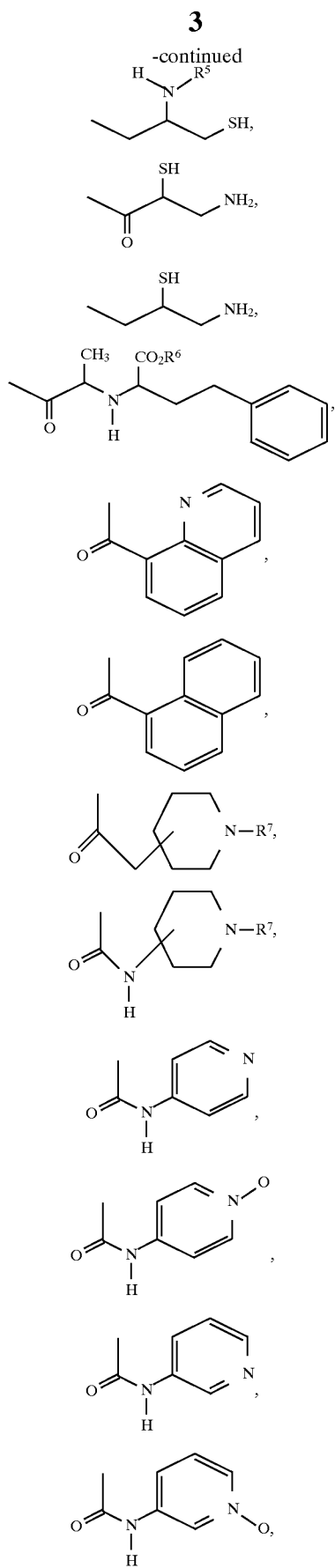
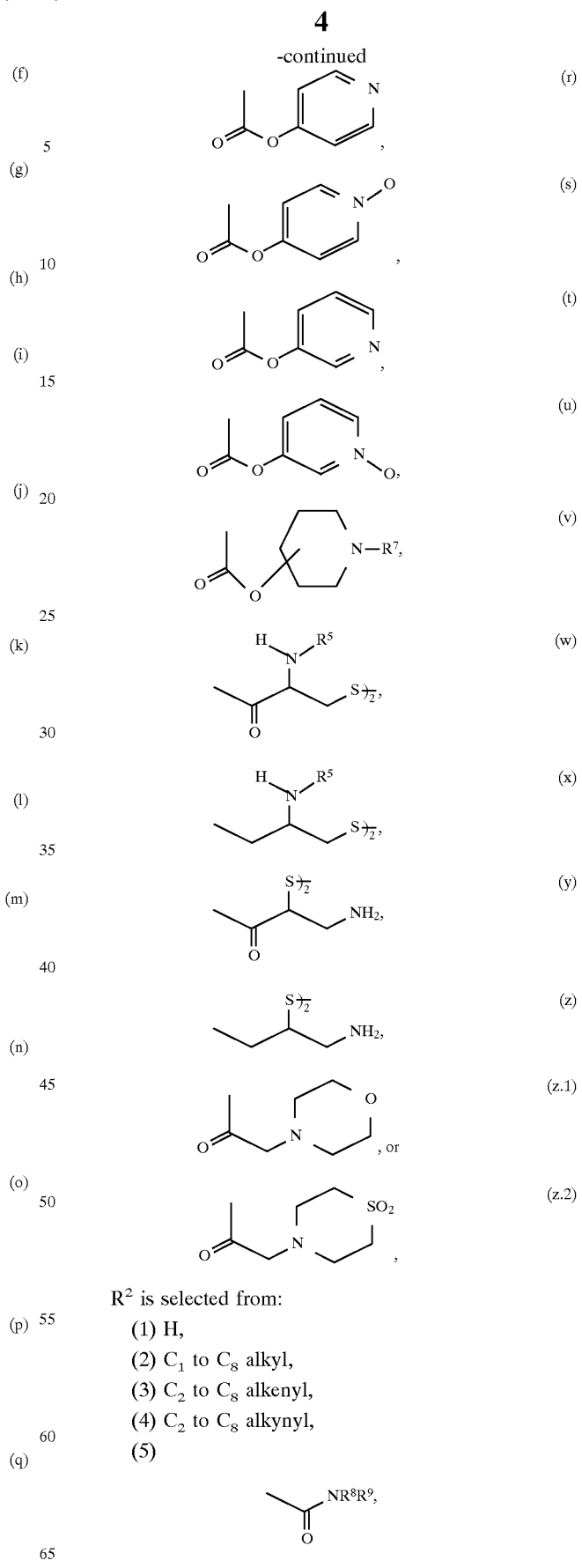
$R^2$ is selected from:
(1) H,
(2) $C_1$ to $C_8$ alkyl,
(3) $C_2$ to $C_8$ alkenyl,
(4) $C_2$ to $C_8$ alkynyl,
(5)
or (6)

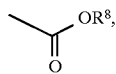

wherein said alkyl, alkenyl, or alkynyl is optionally substituted with one or more groups independently selected from:
(a) aryl, aralkyl, heteroaryl, heteroarylalkyl, or heterocycloalkyl; said aryl, aralkyl, heteroarylalkyl, heteroaryl or heterocycloalkyl optionally substituted with one or more:
  (1) $C_1$ to $C_4$ alkyl,
  (2) $(CH_2)_tOR^8$ wherein t is 1 to 4,
  (3) $(CH_2)_tNR^8R^9$ wherein t is 1 to 4,
  (4) halogen,
(b) $C_3$ to $C_6$ cycloalkyl,
(c) —$OR^8$,
(d) —$SR^8$,
(e) —$S(O)R^8$,
(f) —$SO_2R^8$,
(g) —$NR^8R^9$,
(h)

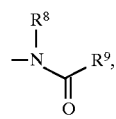

(i)

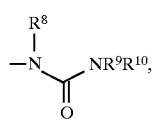

(j)

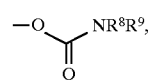

(k)

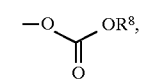

(l)

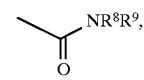

(m)
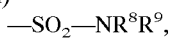
—$SO_2$—$NR^8R^9$,
(n)

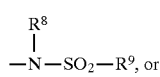

(o)

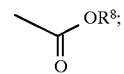

$R^3$ is selected from H, halogen or $C_1$ to $C_6$ alkyl;
$R^4$ is selected from H, halogen or $C_1$ to $C_6$ alkyl;
$R^5$ is selected from: H, $C_1$–$C_6$ alkyl,

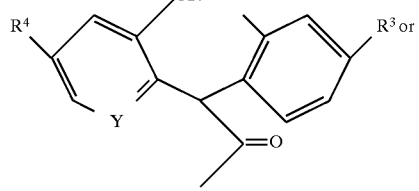

(aa)

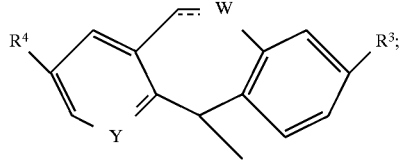

(bb)

$R^6$ is selected from H or $C_1$ to $C_6$ alkyl;
$R^7$ is selected from H, $C_1$ to $C_6$ alkyl, haloalkyl, or —$C(O)R^{11}$ wherein $R^{11}$ is selected from $C_1$ to $C_6$ alkyl, $C_1$ to $C_6$ alkoxy or —$NHR^{12}$ (wherein $R^{12}$ is $C_1$ to $C_6$ alkyl or H), or R7 is an acyl radical of a naturally occurring amino acid;
$R^8$, $R^9$ and $R^{10}$ are independently selected from H, $C_1$ to $C_4$ alkyl, $C_3$ to $C_6$ cycloalkyl, heteroaryl, heteroarylalkyl, heterocycloalkyl, aralkyl, or aryl; said alkyl, cycloalkyl, heteroaryl, heteroarylalkyl, heterocycloalkyl, aralkyl, or aryl are optionally substituted with $C_1$ to $C_4$ alkoxy, aryl, aralkyl, heteroaryl, heteroarylalkyl, cyclopropyl, heterocycloalkyl, halogen, —OH, —$C(O)R^{13}$, —$SO_2R^{13}$, or —$NR^{14}R^{15}$ wherein $R^{13}$ is selected from $C_1$ to $C_4$ alkyl or aralkyl, and wherein $R^{14}$ and $R^{15}$ are independently selected from H, $C_1$ to $C_4$ alkyl or aralkyl, with the provisos that
$R^8$ may not be H in substituents (e), (f), or (k) for $R^2$,
$R^9$ may not be H in substituents (h) or (n) for $R^2$, and
$R^8$, $R^9$, or $R^{10}$ may not be $CH_2OH$ or $CH_2NR^{14}R^{15}$ when $R^{10}$ is directly attached to a heteroatom which is O, S, or N;
$R^{16}$ is selected from H, arylalkyl and $C_1$ to $C_6$ alkyl:
  optionally, when $R^8$ and $R^9$ are bound to the same nitrogen, $R^8$ and $R^9$, together with the nitrogen to which they are bound, form a 5 to 7 membered heterocycloalkyl ring;
  optionally, when $R^9$ and $R^{10}$ are bound to the same nitrogen, $R^9$ and $R^{10}$, together with the nitrogen to which they are bound, form a 5 to 7 membered heterocycloalkyl ring;
- - - - represents an optional bond;
W is selected from CH when the optional bond is present or $CH_2$, O, and S when the optional bond is absent;
X is selected from CH or N;
Y is selected from N or CH: and
Z is selected from —$CO$—$NR^{16}$—, —$NR^{16}$—$CO$—, —$CH_2$—$CH_2$—, and —$CH$=$CH$—.

Preferred groups of compounds of formula 1.0 are those wherein

A. $R^3$ and $R^4$ are halogen, more preferably $R^3$ is Cl and $R^4$ is Br.

B. Y is N.

C. X is N.

D. $R^1$ is selected from formulas (a), (b), (c), (d), (l), (z.1) and (z.2).

E. $R^1$ is selected from formulas (m), (n), (o), (p), (q), (r), (s), (t), (u), and (v).

F. $R^1$ is selected from formulas (e), (f), (g), (h), (w), (x), (y), and (z).

G. $R^1$ is formula (e) or (f) and, more preferably $R^5$ in (e) or (f) is H.

H. $R^2$ is selected from H, $-C_4H_9$, $-CH_2C_6H_5$, $-CH_2CH_2OCH_3$, $-CH_2CH_2SCH_3$, $-CH_2CH_2O-n-C_3H_7$, $-CH_2CH_2CH_2-OCH_3$,

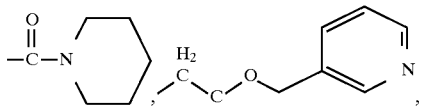

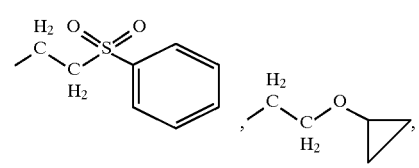

I. W is CH or $CH_2$, Y is N, and X is N. Preferably within this group $R^3$ is Cl and $R^4$ is Br.

J. $R^1$ is

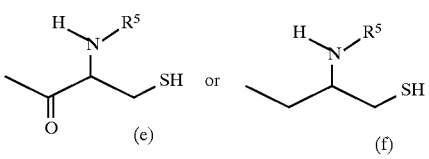

wherein $R^5$ is H, and $R^2$ is selected from H, $-C_4H_9$, $-CH_2C_6H_5$, $-CH_2CH_2OCH_3$, $-CH_2CH_2SCH_3$, $-CH_2CH_2O-n-C_3H_7$, $-CH_2CH_2CH_2OCH_3$,

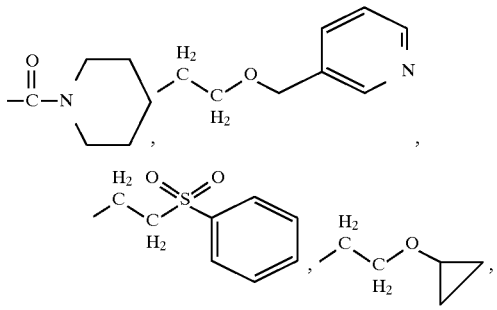

-continued

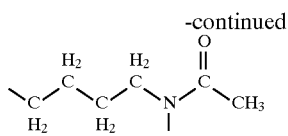 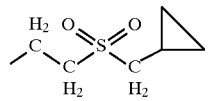

or

The most preferred compounds in this group have the formula

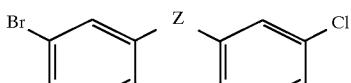

or

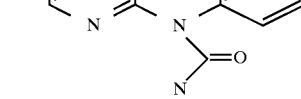

Wherein $R^2$ is H or substituted alkyl and Z is as defined previously

This invention also includes a method for inhibiting the abnormal growth of cells comprising administering an effective amount of a compound of formula 1.0. Preferably the the cells inhibited are tumor cells expressing an activated ras oncogene, or the cells inhibited are pancreatic tumor cells, lung cancer cells, myeloid leukemia tumor cells, thyroid follicular tumor cells, myelodysplastic tumor cells, epidermal carcinoma tumor cells, bladder carcinoma tumor cells or colon tumors cells, or the inhibition of the abnormal growth of cells occurs by the inhibition of ras farnesyl protein transferase, or the inhibition is of tumor cells wherein the Ras protein is activated as a result of oncogenic mutation in genes other than the Ras gene.

Another aspect of this invention is a pharmaceutical composition for inhibiting the abnormal growth of cells comprising an effective amount of compound of formula 1.0 in combination with a pharmaceutically acceptable carrier.

This invention also provides a method for inhibiting tumor growth by administering an effective amount of the tricyclic compounds, described herein, to a mammal (e.g., a human) in need of such treatment. In particular, this invention provides a method for inhibiting the growth of tumors expressing an activated Ras oncogene by the administration of an effective amount of the above described compounds. Examples of tumors which may be inhibited include, but are not limited to, lung cancer (e.g., lung adenocarcinoma), pancreatic cancers (e.g., pancreatic carcinoma such as, for example, exocrine pancreatic carcinoma), colon cancers (e.g., colorectal carcinomas, such as, for example, colon adenocarcinoma and colon adenoma), myeloid leukemias (for example, acute myelogenous leukemia (AML)), thyroid follicular cancer, myelodysplastic syndrome (MDS), bladder carcinoma and epidermal carcinoma.

It is believed that this invention also provides a method for inhibiting proliferative diseases, both benign and malignant, wherein Ras proteins are aberrantly activated as a result of oncogenic mutation in other genes—i.e., the Ras gene itself is not activated by mutation to an oncogenic form—with said inhibition being accomplished by the administration of an effective amount of the tricyclic compounds described herein, to a mammal (e.g., a human) in need of such treatment. For example, the benign proliferative disorder neurofibromatosis, or tumors in which Ras is activated due to mutation or overexpression of tyrosine kinase oncogenes (e.g., neu, src, abl, lck, and fyn), may be inhibited by the tricyclic compounds described herein.

The compounds of this invention inhibit farnesyl protein transferase and the farnesylation of the oncogene protein Ras. This invention further provides a method of inhibiting ras farnesyl protein transferase, in mammals, especially humans, by the administration of an effective amount of the tricyclic compounds described above. The administration of the compounds of this invention to patients, to inhibit farnesyl protein transferase, is useful in the treatment of the cancers described above.

The tricyclic compounds useful in the methods of this invention inhibit the abnormal growth of cells. Without wishing to be bound by theory, it is believed that these compounds may function through the inhibition of G-protein function, such as ras p21, by blocking G-protein isoprenylation, thus making them useful in the treatment of proliferative diseases such as tumor growth and cancer. Without wishing to be bound by theory, it is believed that these compounds inhibit ras farnesyl protein transferase, and thus show antiproliferative activity against ras transformed cells.

DETAILED DESCRIPTION OF THE INVENTION

As used herein, the following terms are used as defined below unless otherwise indicated:

Bu—represents butyl;
Et—represents ethyl;
Me—represents methyl;
Ph—represents phenyl;
Ac—represents $CH_3CO$;
TMS—represents trimethylsilyl;
BOC—represents tert-butoxycarbonyl;
Tr—represents triphenylmethyl [trityl];
Cbz represents benzyloxycarbonyl;

Except where stated otherwise, the following definitions apply throughout the specification and claims. These definitions apply regardless of whether a term is used by itself of in combination with other terms. Hence, for example, the definition of "alkyl" applies to "alkyl" as well as the alkyl portions of "alkoxy, haloalkyl", etc.:

alkyl—represents straight and branched carbon chains and contains from one to twenty carbon atoms, preferably one to six carbon atoms;

alkanediyl—represents a divalent, straight or branched hydrocarbon chain having from 1 to 20 carbon atoms, preferably 1 to 6 carbon atoms, the two available bonds being from the same or different carbon atoms thereof, e.g., methylene, ethylene, ethylidene, —$CH_2CH_2CH_2$—, —$CH_2CHCH_3$, —$CHCH_2CH_3$, etc.

cycloalkyl—represents saturated carbocyclic rings branched or unbranched of from 3 to 20 carbon atoms, preferably 3 to 7 carbon atoms;

heterocycloalkyl—represents a saturated, branched or unbranched carbocylic ring containing from 3 to 15 carbon atoms, preferably from 4 to 6 carbon atoms, which carbocyclic ring is interrupted by 1 to 3 hetero groups selected from —O—, —S— or —$NR^{10}$- (suitable heterocycloalkyl groups including 2- or 3-tetrahydrofuranyl, 2- or 3-tetrahydrothienyl, 2-, 3- or 4-piperidinyl, 2- or 3-pyrrolidinyl, 2- or 3-piperizinyl, 2- or 4-dioxanyl, etc.);

alkenyl—represents straight and branched carbon chains having at least one carbon to carbon double bond and containing from 2 to 12 carbon atoms, preferably from 2 to 6 carbon atoms and most preferably from 3 to 6 carbon atoms;

alkynyl—represents straight and branched carbon chains having at least one carbon to carbon triple bond and containing from 2 to 12 carbon atoms, preferably from 2 to 6 carbon atoms;

aryl—represents a carbocyclic group containing from 6 to 15 carbon atoms and having at least one aromatic ring (e.g., aryl is a phenyl ring), with all available substitutable carbon atoms of the carbocyclic group being intended as possible points of attachment, said carbocyclic group being optionally substituted (e.g., 1 to 3) with one or more of halo, alkyl, hydroxy, alkoxy, phenoxy, $CF_3$, amino, alkylamino, dialkylamino, —$COOR^{10}$ or —$NO_2$; and halo—represents fluoro, chloro, bromo and iodo; and heteroaryl—represents cyclic groups, optionally substituted with $R^3$ and $R^4$, having at least one heteroatom selected from O, S or N, said heteroatom interrupting a carbocyclic ring structure and having a sufficient number of delocalized pi electrons to provide aromatic character, with the aromatic heterocyclic groups preferably containing from 2 to 14 carbon atoms, e.g., triazolyl, 2-, 3- or 4-pyridyl or pyridyl N-oxide (optionally substituted with $R^3$ and $R^4$), wherein pyridyl N-oxide can be represented as:

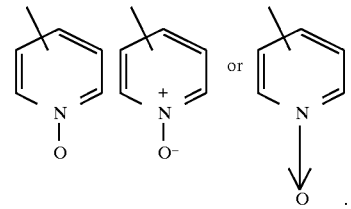

The term "acyl radical of a naturally occuring amino acid" means a group of the formula —C(O)—$R^{29}$, wherein $R^{29}$ is a group of the formula

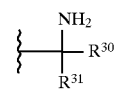

wherein $R^{30}$ and $R^{31}$ are independently selected from H, alkyl, or M-substituted alkyl, wherein M is HO—, HS—, CH₃S—, —NH₂, phenyl, p-hydroxyphenyl, or indolyl, such that HO—C(O)—R²⁹ is an amino acid selected from alanine, glycine, valine, leucine, isoleucine, phenylalanine, trytophan, methionine, serine, theronine, cysteine, cystine, or tyrosine.

The following solvents and reagents are referred to herein by the abbreviations indicated: tetrahydrofuran (THF); ethanol (EtOH); methanol (MeOH); acetic acid (HOAc or AcOH); ethyl acetate (EtOAc); N,N-dimethylformamide (DMF); trifluoroacetic acid (TFA); trifluoroacetic anhydride (TFAA); 1-hydroxybenzotriazole (HOBT); m-chloroperbenzoic acid (MCPBA); triethylamine (Et₃N); diethyl ether (Et₂O); ethyl chloroformate (ClCO₂Et); 1-(3-dimethylaminopropyl)-3-ethyl carbodiimde hydrochloride (DEC); 1-8-diazabicyclo[5.4.0]undec-7-ene (DBU); N-bromosuccinimide (NBS).

Lines drawn into the ring systems indicate that the indicated bond may be attached to any of the substitutable ring carbon atoms.

Certain compounds of the invention may exist in different isomeric (e.g., enantiomers and diastereoisomers) forms. The invention contemplates all such isomers both in pure form and in admixture, including racemic mixtures. Enol forms are also included.

Certain tricyclic compounds will be acidic in nature, e.g. those compounds which possess a carboxyl or phenolic hydroxyl group. These compounds may form pharmaceutically acceptable salts. Examples of such salts may include sodium, potassium, calcium, aluminum, gold and silver salts. Also contemplated are salts formed with pharmaceutically acceptable amines such as ammonia, alkyl amines, hydroxyalkylamines, N-methylglucamine and the like.

Certain basic tricyclic compounds also form pharmaceutically acceptable salts, e.g., acid addition salts. For example, the pyrido-nitrogen atoms may form salts with strong acid, while compounds having basic substituents such as amino groups also form salts with weaker acids. Examples of suitable acids for salt formation are hydrochloric, sulfuric, phosphoric, acetic, citric, oxalic, malonic, salicylic, malic, fumaric, succinic, ascorbic, maleic, methanesulfonic and other mineral and carboxylic acids well known to those in the art. The salts are prepared by contacting the free base form with a sufficient amount of the desired acid to produce a salt in the conventional manner. The free base forms may be regenerated by treating the salt with a suitable dilute aqueous base solution such as dilute aqueous NaOH, potassium carbonate, ammonia and sodium bicarbonate. The free base forms differ from their respective salt forms somewhat in certain physical properties, such as solubility in polar solvents, but the acid and base salts are otherwise equivalent to their respective free base forms for purposes of the invention.

All such acid and base salts are intended to be pharmaceutically acceptable salts within the scope of the invention and all acid and base salts are considered equivalent to the free forms of the corresponding compounds for purposes of the invention.

Compounds containing methiol (—SH group) may oxidize to the disulfide group (—S—S—) and such disulfide compounds are also part of this invention. An example of a disulfide compound in accordance with this invention would be

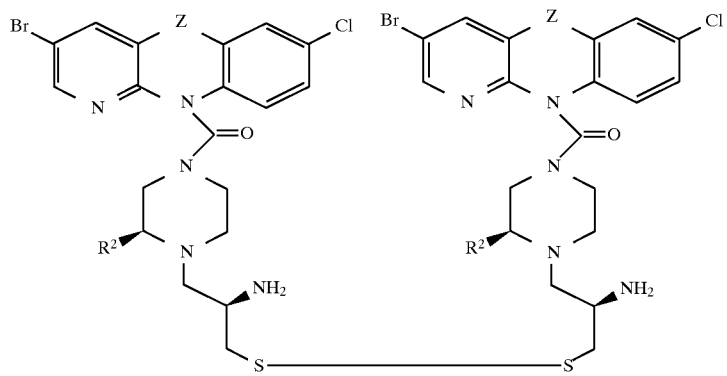

Compounds containing the thiol group may be converted to disulfide compounds and vice versa as shown in the examples.

Compounds of Formula 1.0 can be produced by the following processes:

Process A

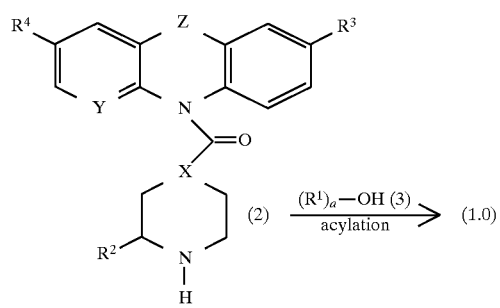

Wherein $(R^1)_a$ is a group $R^1$ in accordance with formulas (a)–(e), (g), (i)–(l), (w), (y), (z.1) or (z.2). Process A is carried out in solvent e.g. DMF at 0° to 60° C. for 1–70 hours.

Process B

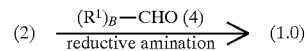

Wherein $(R^1)_B$ is a group $R^1$ in accordance with formulas (f), (h), (x) or (z).

Process B is carried out in solvent such as DMF at 0°–60° C. at pH of 5–6 in the presence of a proton source, e.g. mineral acid or trifluoroacetic acid, and a reducing agent, e.g. sodium triacetoxyborohydride or sodium cyanoborohydride for 1–70 hours.

Process C (2) 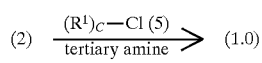 (1.0)

Wherein $(R^1)_C$ is a group $R^1$ in accordance with formula (r)–(v). Process C is carried out in solvent such as dichloromethane at 0°–60° C. for 1–70 hours.

Process D (2) 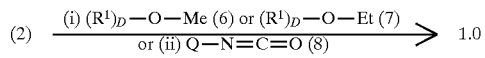 1.0

Wherein $(R^1)_D$ is a group $R^1$ in accordance with formulas (m)–(q) and wherein Q is a group $R^1$ of formulas (m)–(q) except that the —C(O)NH group is absent. Process D is carried out in (i) without any added solvent, as a melt of the reactants at 130°–180° C. for from 1–24 hours. Process D is carried out in (ii) using anhydrous toluene as the solvent at from 0°–30° C. for 16–120 hours.

Processes A, B, C, or D are followed if necessary or desired by removal of any protective groups, conversion of a compound for formula (1.0) to a different compound of formula (1.0) or converting the compound of formula (1.0) to its pharmaceutically acceptable salt, acid addition salt, base salt, or disulfide.

Intermediate compounds 2, 3, 4, 5, 6, 7, and 8 are known or can be produced as illustrated in the following examples.

In these processes, it is sometimes desirable and/or necessary to protect certain groups during the reactions. Conventional protecting groups are operable as described in Greene, T. W., "Protective Groups In Organic Synthesis", John Wiley & Sons, New York, 1981. For example, the groups listed in column 1 of Table A may be protected as indicated in column 2 of the table:

TABLE 1
PROTECTED GROUPS

| 1. GROUP TO BE PROTECTED | 2. PROTECTED GROUP |
|---|---|
| —COOH | —COOalkyl, —COObenzyl, —COOphenyl, 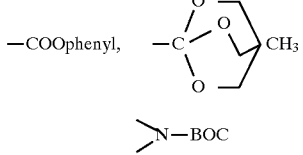 |
| >NH | >N—BOC, >N—Cbz |
| >CO | 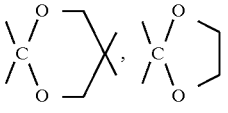 |
| —OH | 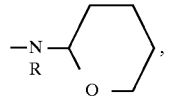, —OCH$_2$phenyl, —OCH$_3$, OSi(CH$_3$)$_2$(t-Bu) |

TABLE 1-continued
PROTECTED GROUPS

| 1. GROUP TO BE PROTECTED | 2. PROTECTED GROUP |
|---|---|
| —NHR, wherein R is any substituent on an amino group within the scope of the claims | 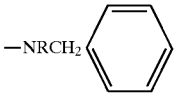, —NR—CO—CF$_3$, —NRCOCH$_3$, —NRCH$_2$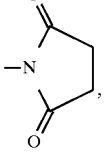 |
| —NH$_2$ | 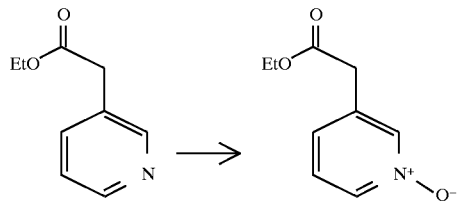, —NH—C(O)—O(t-Bu) |

Other protecting groups well known in the art also may be used. After the reaction or reactions, the protecting groups may be removed by standard procedures.

Compounds useful in this invention are exemplified by the following preparative examples, which should not be construed to limit the scope of the disclosure. Alternative mechanistic pathways and analogous structures within the scope of the invention may be apparent to those skilled in the art.

PREPARATIVE EXAMPLE 1

A. ETHYL 3-PYRIDYLACETIC ACID 1-N-OXIDE

Ethyl 3-pyridylacetic acid (10 grams) (60.6 mmoles) was dissolved in dry CH$_2$Cl$_2$ (120 ml) and the solution was stirred at −18° C. for 30 minutes. MCPBA (31.34 grams) (181.6 mmoles) was added and the mixture was stirred at −18° C. for 1 hour and then at 25° C. for 87 hours. The reaction mixture was diluted with CH$_2$Cl$_2$ and washed with saturated aqueous sodium bicarbonate and then water. The CH$_2$Cl$_2$ was then dried (magnesium sulphate), filtered and evaporated to dryness. The residue was chromatographed on silica gel using 3% (10% concentrated ammonium hydroxide in MeOH)—CH$_2$Cl$_2$ as the eluant to give the product compound (Yield: 8.45 grams, 77%, MH$^+$ 182).

B. 3-PYRIDYLACETIC ACID 1-N-OXIDE

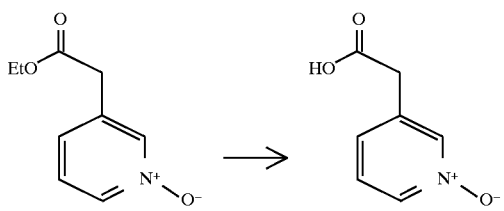

Ethyl 3-Pyridylacetic acid 1-N-oxide (0.2747 grams) (1.5 mmoles) was dissolved in EtOH (200 proof) (1.22 ml.) and a 1M solution of LiOH in water (3.64 ml.) (3.0 mmoles) was added and the mixture was stirred at 25° C. for 4 hours. 1N HCl (4.28 ml.) was added and the mixture was pumped down to dryness on a rotary evaporator to give the product compound (Yield: 0.2931 grams, 100%).

PREPARATIVE EXAMPLE 2

A. ETHYL α-METHYL-3-PYRIDYLACETIC ACID.

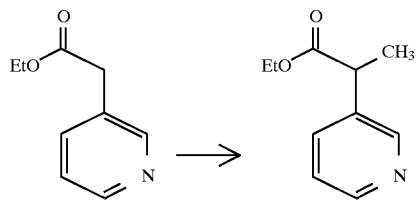

To ethyl 3-pyridylacetic acid (10.86 grams) (65.7 mmoles) was added a 2.0M solution of lithium diisopropylamide in THF/heptane/ethyl benzene (32.87 ml.) (65.8 mmoles) at −30° C. The semi-solid mixture was agitated and sonicated for 1 hour. The mixture was allowed to remain at 25° C. for 1 hour, whereupon methyl iodide (4.09 ml.) (65.7 mmoles) was added. After 1 hour at 25° C. the mixture was taken up in $CH_2Cl_2$ and washed with saturated aqueous sodium bicarbonate and water. The $CH_2Cl_2$ was dried (magnesium sulphate), filtered and evaporated to dryness. The residue was chromatographed on silica gel using 10% EtOAc in hexane as the eluant to give the product compound (Yield: 3.48 grams, 30%, MH+ 180).

B. α-METHYL-3-PYRIDYLACETIC ACID.

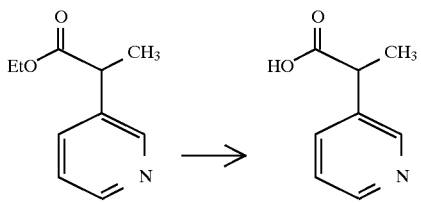

The product compound from Preparative Example 2A above (2.16 grams) (12.05 mmoles) was dissolved in EtOH (10 ml.) and 1.0M LiOH in water (29.15 ml.) (29.2 mmoles) was added. The mixture was stirred at 25° C. for 4 hours, whereupon 1N HCl (34.27 ml.) (34.2 mmoles) was added and the solution was evaporated to dryness to give the product compound (Yield 2.33 grams, 100%).

PREPARATIVE EXAMPLE 3

α,α-DIMETHYL-3-PYRIDYLACETIC ACID.

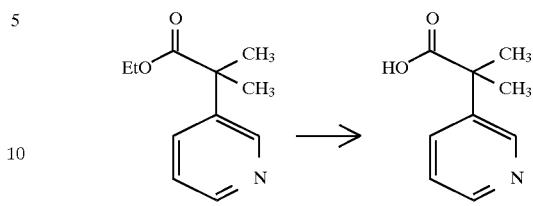

Ethyl α,α-dimethyl-3-pyridylacetate (disclosed in EP Application 0 288 279, published Oct. 26, 1988) (2.67 grams, 13.8 mmoles) was dissolved in EtOH (11.1 ml.) and a 1.0M LiOH in water (33.3 ml.) (33.4 mmoles) was added. The mixture was stirred at 25° C. for 4 hours. 1N HCl (38.73 ml.) was added and after 5 minutes the mixture was evaporated to dryness to give the titlle compound (Yield: 100%).

PREPARATIVE EXAMPLE 4

4-ETHOXYCARBONYLAMINOPYRIDINE

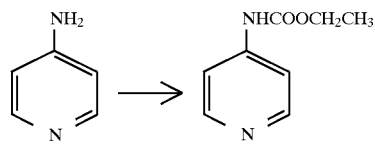

4-Aminopyridine (17.34 grams) (184.3) was dissolved in dry pyridine (217 ml.) and cooled to 0° C. over 30 minutes. Ethyl chloroformate (17.2 ml.) (180.7 mmoles) was added and the solution was stirred at 0° C. for 1 hour and then at 25° C. for 40 hours. The mixture was diluted with $CH_2Cl_2$ and washed with saturated aqueous $NaHCO_3$ and water. The $CH_2Cl_2$ was dried ($MgSO_4$), filtered and evaporated to dryness. The residue was chromatographed on silica gel using 2% (10% saturated $NH_4OH$ in MeOH)—$CH_2Cl_2$ to give the product compound (Yield: 10 grams, 33%, M+ 166).

By using essentially the same procedure, with the exception that

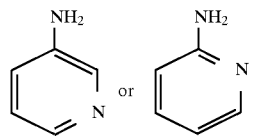

was used instead of 4-aminopyridine, the compound

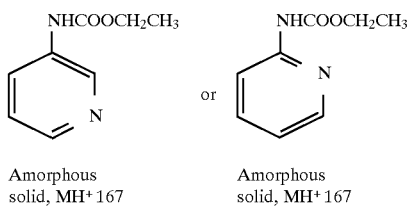

| Amorphous solid, MH+ 167 | Amorphous solid, MH+ 167 | was obtained, respectively.

PREPARATIVE EXAMPLE 5
A. N-ACETYLISONIPECOTIC ACID

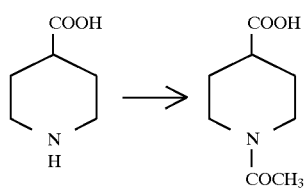

Isonipecotic acid (10 grams) (77.5 mmoles) and acetic anhydride (23.7 grams) (232.5 mmoles) were dissolved in MeOH (100 ml.) and the mixture was stirred at 25° C. for 24 hours. The mixture was evaporated to dryness and the residue was azeotroped with toluene to give the product compound (Yield: 12.8 grams, 97%, MH$^+$ 172).

B. 1-N-tert-BUTOXYCARBONYLISONIPECOTIC ACID

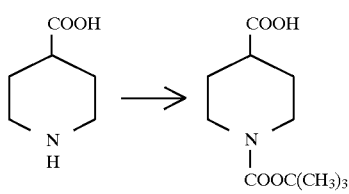

Isonipecotic acid (20 grams) (155.0 mmoles) was dissolved in THF-water (1:1) (400 ml) and NaOH (6.2 grams) (155.0 mmoles) and di-tert-butyldicarbonate (37.2 grams) (170.5 mmoles) were added. The mixture was stirred at 25° C. for 72 hours. The solution was then eluted through a bed of washed BioRad 50WX4 (RSO3H resin) (150 ml bed) and the resin was eluted with a 1:1 mixture of THF and water. The eluate was evaporated to dryness to give the product compound (Yield: 33.78 grams, 90%).

PREPARATIVE EXAMPLE 6
1-N-ACETYLNIPECOTIC ACID

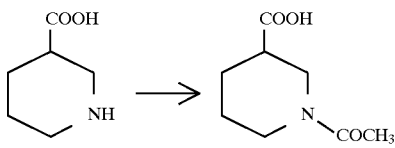

Nipecotic acid (3.87 grams) (30.0 mmoles) was reacted with acetic anhydride (9.17 grams) (90 mmoles) as described in Preparative Example 5A to give the product compound (Yield: 5.0 grams, 97%, MH$^+$ 172).

PREPARATIVE EXAMPLE 7
1-N-METHYLNIPECOTIC ACID

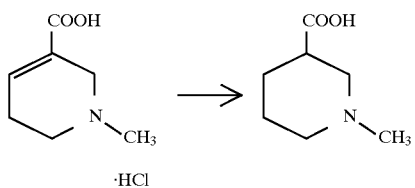

Arecaidine hydrochloride (4 grams) (22.6 mmoles) was hydrogenated in water (100 ml) using 10% Pd-C at 40 psi at 25° C. for 24 hours. The catalyst was filtered off and washed with water. The aqueous solution was shaken with BioRad AG1X8 resin (OH$^-$ form) (23 ml bed) and after 5 minutes the resin was filtered off and washed with water. The aqueous solution was evaporated to give the product compound (Yield: 2.95 grams, 92%).

PREPARATIVE EXAMPLE 8
1-N-ACETYL D,L-PIPECOLINIC ACID

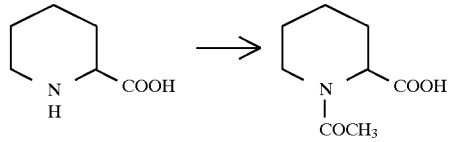

D,L-Pipecolinic acid (10 grams) (77.5 mmoles) and acetic anhydride (23.7 grams) (232.5 mmoles) were reacted as described in Preparative Example 5A above to give the product compound (Yield: 12.94 grams, 98%, MH$^+$ 172).

PREPARATIVE EXAMPLE 9
A. PIPERIDINE-4-ACETIC ACID

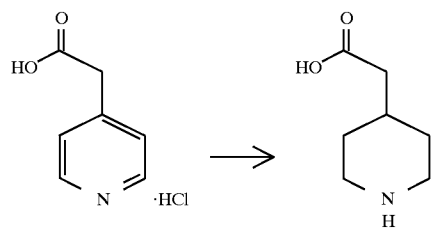

4-Pyridylacetic acid (7 grams) (40.4 mmoles) was hydrogenated as described in Preparative Example 7 to give the product compound (Yield: 5.2 grams, 90%, MH$^+$ 144).

B. 1-N-ACETYL-4-PIPERIDINYLACETIC ACID

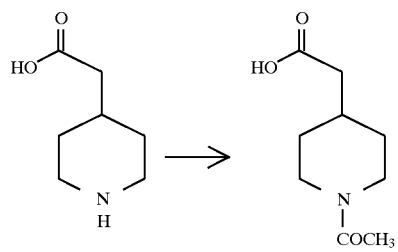

4-Piperidinylacetic acid (5 grams) (35.0 mmoles) was reacted with acetic anhydride (10.7 grams) (105.0 mmoles) as described in Preparative Example 5A to give the product compound (Yield: 6.4 grams, 99%, MH$^+$ 185).

C. 1-N-METHYL-4-PIPERIDINYLACETIC ACID

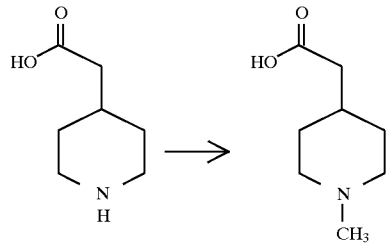

4-Piperidinylacetic acid (4 grams) (28.0 mmoles) from Preparative Example 9A was dissolved in water (50 ml) and 37% formalin (2.72 ml) (33.6 mmoles) was added. The mixture was hydrogenated over 10% Pd-C at 55 psi at 25°

C. for 68 hours. The catalyst was filtered off and washed with water. The combined filtrates were evaporated to dryness to give the product compound (MH+ 158).

D. 1-N-tert-BUTOXYCARBONYLPIPERIDINYL-4-ACETIC ACID

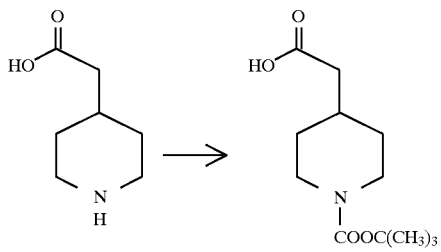

4-Piperidinylacetic acid (41.24 grams) (288.4 mmoles) from Preparative Example 9A was reacted with di-tert-butyldicarbonate (69.14 grams) (317.3 mmoles) and NaOH (11.52 grams) (288.4 mmoles) as described in Preparative Example 5B above to give the product compound (Yield: 53.0 grams, 76%).

PREPARATIVE EXAMPLE 10

A. 3-PIPERIDINYLACETIC ACID

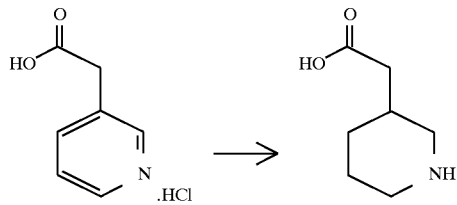

3-Pyridylacetic acid hydrochloride (13 grams) (74.9 mmoles) was hydrogenated as described in Preparative Example 7 to give a mixture of unreacted 3-pyridylacetic acid and the product compound (76:24) (8.63 grams, MH+ 144).

B. 1-N-ACETYL-3-PIPERIDINYLACETIC ACID

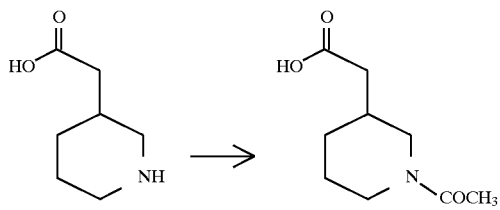

The mixture of compounds from Preparative Example 10A (8.56 grams) were reacted with acetic anhydride (8.56 grams) as described in Preparative Example 5A and the crude mixture of products was taken up in MeOH (60 ml) and passed over a bed of BioRad AG50WX4 resin (RSO$_3$H) and the latter was eluted with MeOH. The eluates were evaporated to dryness to give the product compound (Yield: 1.23 grams, MH+ 186).

C. 1-N-METHYL-3-PIPERIDINYLACETIC ACID

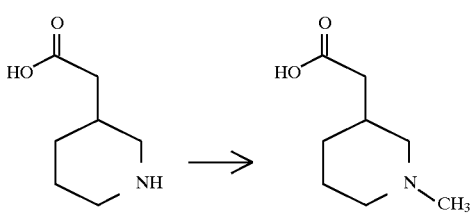

The mixture of compounds from Preparative Example 10A (4 grams) and 37% formalin (2.72 ml.) were hydrogenated as described in Preparative Example 9C to give the product compound (MH+ 158).

PREPARATIVE EXAMPLE 11

A. ETHYL α-METHYL-4-PYRIDYL ACETIC ACID

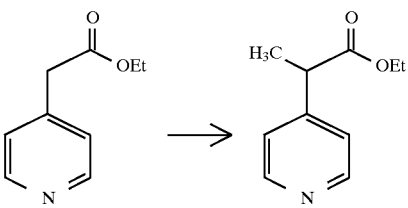

To dry THF at −78° C. was added diisopropylamine(5.05 g 48 mmol, 7 mL) and then n-butyl lithium. The reaction mixture was stirred for 0.5 h and then ethyl 4-pyridyl acetic acid (7.85 g, 46 mmol) was added, and after stirring for 0.5 h at that −78° C. the reaction temperature was raised to room temperature. DMF (20 mL was added and the reaction mixture cooled to −78° C. again. Methyl iodide(7.07 g, 50.2 mmol, 3.15 mL) was added and the reaction mixture stirred at that temperature for 1 h and then at room temperature overnight. All the volatiles were then stripped off and the reaction mixture was partitioned between water-CH$_2$Cl$_2$. The aqueous phase was washed twice with CH$_2$Cl$_2$. The combined CH$_2$Cl$_2$ phases were dried and evaporated. The crude product was chromatographed on silica gel eluting with 80% EtOAc hexane to give the product compound (7.88 g, MH+ 179).

B. α-METHYL-4-PYRIDYL ACETIC ACID

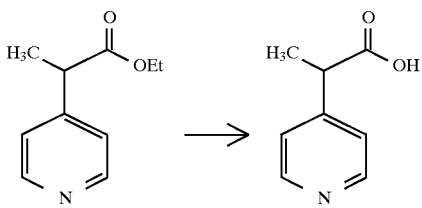

The compound from Preparative Example 11A was hydrolysed in a similar manner to Preparative Example 2B to give the product compound (MH+ 152).

PREPARATIVE EXAMPLE 12

A.–B. α,α-DIMETHYL-4-PYRIDYL ACETIC ACID

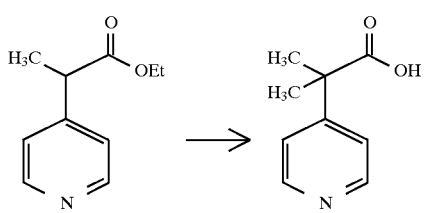

By essentialy the same procedure as set forth in Preparative Example 2A, but using ethyl α-methyl-4-pyridylacetic acid (from Preparative Example 11A) instead of ethyl 3-pyridyl acetic acid the product compound was obtained as an oil (MH⁺ 166).

PREPARATIVE EXAMPLE 13

3-PYRIDYLISOCYANATE, HYDROCHLORIDE

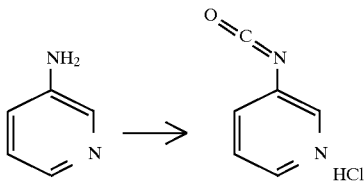

A 1.93 solution of phosgene in toluene (20%) (584 mL) was diluted with dry $CH_2Cl_2$ (1 L) and the mixture was stirred at 0° C. under nitrogen atmosphere. A solution of 3-aminopyridine (21.1 grams) and dry pyridine (19 mL) dissolved in dry $CH_2Cl_2$ (600 mL) was added dropwise to the stirred solution at 0° C. over a period of 5.5 hours. The mixture was stirred at 0°–25° C. for an additional 48 hours. A stream of nitrogen was passed through the solution to remove most of the phosgene and the solution was then evaporated until almost all of the solvent was removed to give the product compound which was then taken up in dry pyridine (850 mL) to give a stock solution of the product compound.

PREPARATIVE EXAMPLE 14

A. ETHYL α,α-DIMETHYL-3-PYRIDYLACETIC ACID N-OXIDE

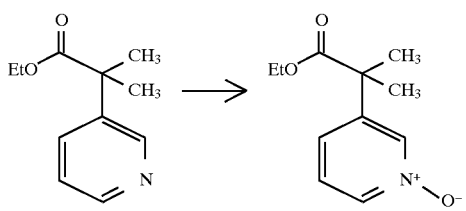

By substituting in Preparative Example 1A, ethyl α,α-dimethyl-3-pyridylacetic acid (4.0 g, 20.7 mmoles) for ethyl 3-pyridylacetic acid and using the same method as described in Preparative Example 1A, one obtains the product compound (3.2 g, 74%, MH⁺ 210).

B. α,α-DIMETHYL-3-PYRIDYLACETIC ACID N-OXIDE

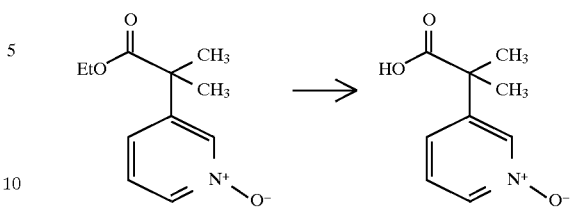

By substituting in Preparative Example 1B, ethyl α,α-dimethyl-3-pyridylacetic acid N-oxide (0.142 g, 0.68 mmoles) (Preparative Example 14A) for ethyl 3-pyridylacetic acid N-oxide and using the same method as described in Preparative Example 1B, one obtains the product compound.

PREPARATIVE EXAMPLE 15

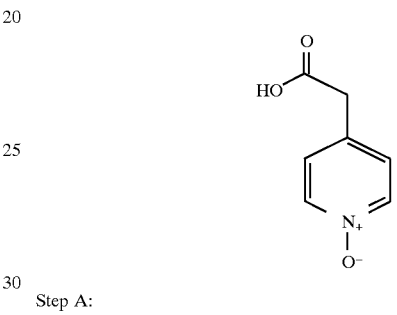

Step A:

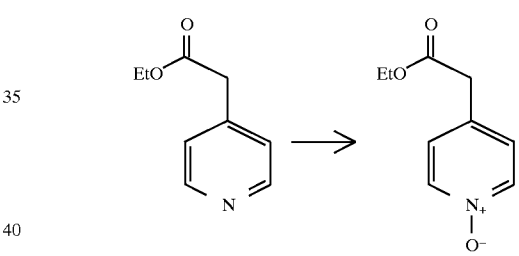

Combine 10 g (60.5 mmol) of ethyl 4-pyridylacetate and 120 mL of dry $CH_2Cl_2$ at −20° C. Add 10.45 g (60.5 mmol) of MCPBA and stir at −20° C. for 1 hour and then at 25° C. for 67 hours. Add an additional 3.48 g (20.2 mmoles) of MCPBA and stir at 25° C. for 24 hours. Dilute with $CH_2Cl_2$ and wash with saturated $NaHCO_3$ (aqueous) and then water. Dry over $MgSO_4$, concentrate in vacuo to a residue, and chromatograph (silica gel, 2%–5.5% (10% $NH_4OH$ in MeOH)/$CH_2Cl_2$)to give 8.12 g of the product compound. Mass Spec.: MH⁺=182.15

Step B:

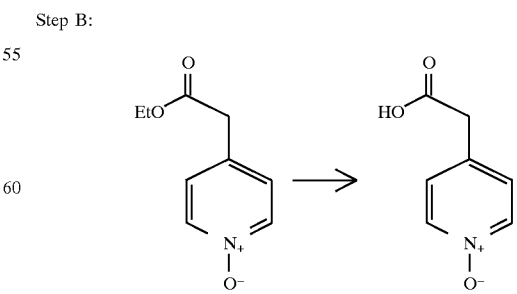

Combine 3.5 g (19.3 mmol) of the product of Step A, 17.5 mL of EtOH and 96.6 mL of 10% NaOH (aqueous) and heat the mixture at 67° C. for 2 hours. Add 2N HCl (aqueous) to adjust to pH=2.37 and concentrate in vacuo to a residue. Add 200 mL of dry EtOH, filter through Celite® and wash the filter cake with dry EtOH (2×50 ml). Concentrate the combined filtrates in vacuo to give 2.43 g of the product compound.

PREPARATIVE EXAMPLE 16

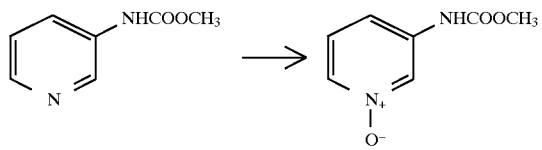

Combine 10 g (65.7 mmol) of 3-methoxycarbonylaminopyridine and 150 mL of CH$_2$Cl$_2$, cool to 0° C. and slowly add (dropwise) a solution of 13.61 g (78.84 mmol) of MCPBA in 120 mL of CH$_2$Cl$_2$ at 0° C. over a period of 1 hour. Stir the mixture at 25° C. for 5 days, then wash with saturated NaHCO$_3$ (aqueous), then water and dry over MgSO$_4$. Concentrate in vacuo to a residue and chromatograph (silica gel, 2%–5% (10% NH$_4$OH in MeOH) /CH$_2$Cl$_2$) to give the product compound. Mass Spec.: MH$^+$= 169

PREPARATIVE EXAMPLE 17 AND 17A

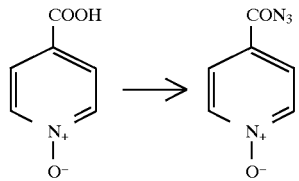

Combine 5 g (36.0 mmol) of isonicotinic acid 1-N-oxide and 150 mL of anhydrous DMF, add 5.5 mL (39.6 mmol) of Et$_3$N and stir at 0° C. for 0.5 hours. Slowly add (dropwise) 8.5 mL (39.6 mmol) of diphenylphosphoryl azide at 0° C. over 10 minutes, stir at 0° C. for 1 hour and then at 25° C. for 24 hours (as generally described in Pavia, et al, *Journal of Medicinal Chemistry*, 33, 854–861 (1990)). Concentrate in vacuo to a residue and chromatograph (silica gel, 0.5%–1% MeOH/CH$_2$Cl$_2$) to give 5.9 g of the product compound.

Using nicotinic acid 1-N-oxide and substantially the same procedure as described for Preparative Example 17 the following compound was prepared:

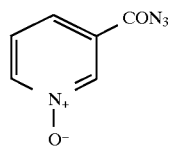 (17A)

PREPARATIVE EXAMPLE 18

Step A:

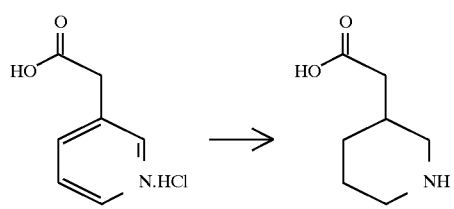

Hydrogenate 25 g (144 mmol) of 3-pyridylacetic acid hydrochloride for 144 hours using the procedure described in Preparative Example 7 and allowing the reaction to proceed for 144 hours, to give 20 g of the product compound. Mass Spec.: MH$^+$=144.

Step B:

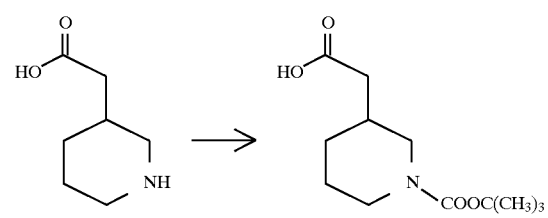

React 12 g (83.8 mmol) of the product of Step A for 148 hours using the procedure described in Preparative Example 5, Step B, to give 17.5 g of the product compound. Mass Spec.: MH$^+$=244.25

PREPARATIVE EXAMPLE 19

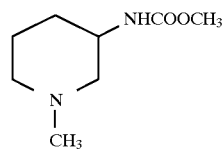

Combine 25 g (164.4 mmol) of methyl 3-pyridylcarbamate and 163.3 mL of 1N HCl (aqueous), stir until all of the solid dissolves, then hydrogenate over 10% Pd/C at 25° C. at 55 psi for 220 hours. Filter, wash the solids with water and treat the combined filtrates with 150 mL of BioRad AG1X8 ion exchange resin (OH$^-$). Filter, wash the resin with water and concentrate the filtrate to a volume of 100 mL. Add 16.43 mL (197.3 mmol) of 37% formalin and hydrogenate over 10% Pd/C at 25° C. at 55 psi for 89 hours. Filter, wash the solids with water and concentrate in vacuo to give 24.3 g of the product compound. Mass Spec.: MH$^+$=173.2

PREPARATIVE EXAMPLE 20

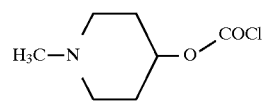

Combine 10 mL of dry CH$_2$Cl$_2$ and 914.6 mL (28.1 mmol) of a 1.93M solution of phosgene in toluene, cool to 0° C. and slowly add (dropwise) a solution of 0.6484 g (5.62 mmol) of 4-hydroxy-1-N-methylpiperidine, 1.214 mL (15 mmol) of pyridine and 10 mL of dry CH$_2$Cl$_2$ over 10 min., then stir at 0°–25° C. for 2 hours. Purge excess phosgene with N$_2$ then concentrate in vacuo to give the product compound.

EXAMPLE 1

Preparation of:

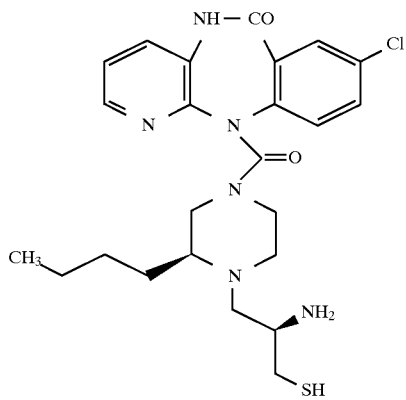

STEP A

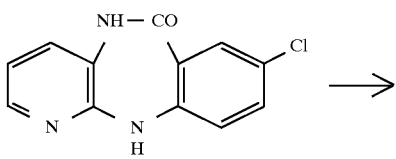

The reactant prepared by the method described in either, W. W. Engel, et al., J. Med. Chem., 1989, 32,1718–1724, or M. Oklobdzija, et al., J. Heterocyclic Chemistry, 20, 1329–1334 (1983), is dissolved in anhydrous dichloromethane and an excess of a 1M solution of phosgene in toluene is added. After 1 hour the excess phosgene is removed and the solution evaporated to dryness to give the product compound which is used without further purification.

STEP B

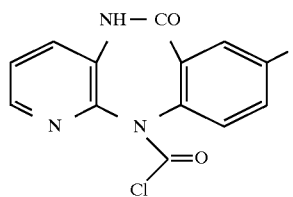

-continued
STEP B

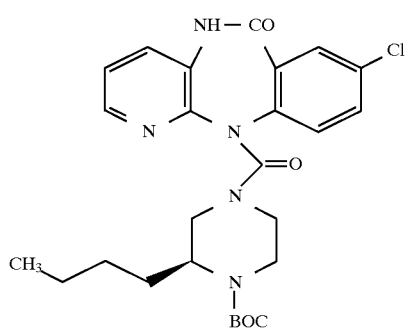

The product chloroformate from Step A above is reacted with 1-tert-butoxycarbonyl2(S)n-butylpiperazine (prepared as described in Example 3C WO 95/00497) in the presence of triethylamine in dichloromethane at room temperature to afford the product compound which may be purified in the usual manner.

STEP C

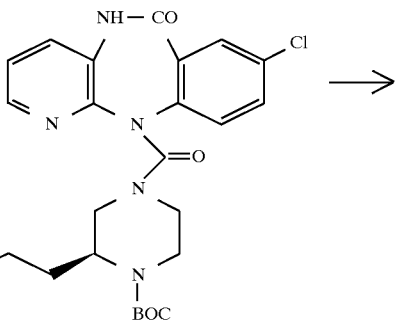

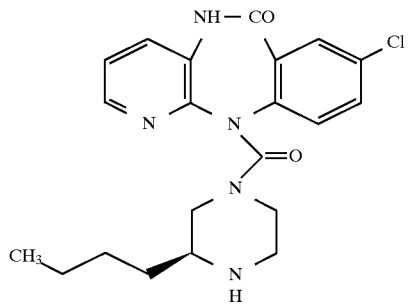

The product compound from Step B above is dissolved in methanol and a 10% (v/v) concentrated sulfuric acid in dioxane solution is added and the mixture is stirred at 25° C. for 2 hrs. The mixture is neutralized with BioRad AG1X8 (OH$^-$) resin and filtered. The resin is washed methanol and dichloroethane and the combined filtrates are evaporated to dryness to give the product compound. The latter is purified on a silica gel column using 3%–5% (10% concentrated ammonium hydroxide in methanol)-dichlormethane to give the product compound.

STEP D

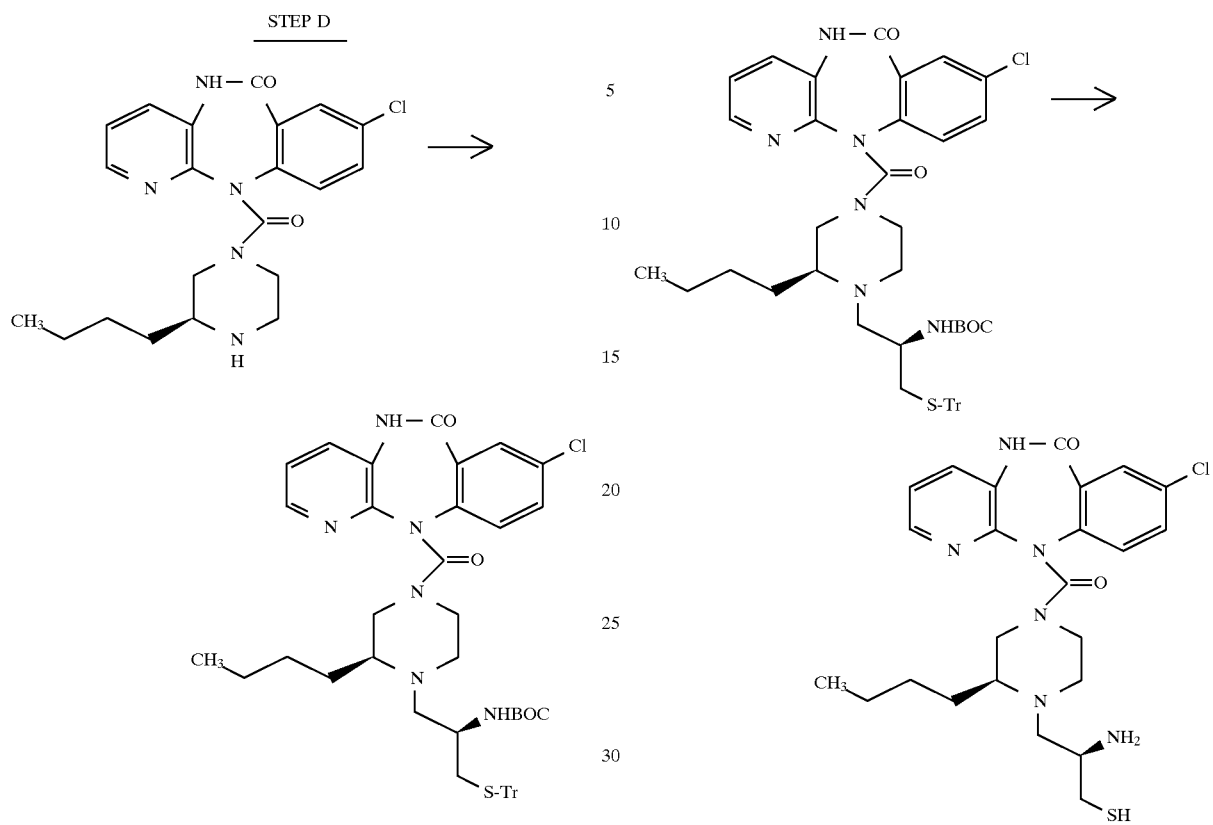

STEP E

The product compound from Step C is dissolved in a saturated solution of dry hydrogen chloride gas in anhydrous dichloromethane, or alternatively in trifluoroacetic acid in dichloromethane, and the mixture is stirred at 25° C. for 5 minutes. Evaporation to dryness afforded the acid addition salt. The acid addition salt is dissolved in anhydrous dimethylformamide and sodium triacetoxyborohydride, or alternatively sodium cyanoborohydride, and crushed 3 Å molecular sieves are added and the mixture is stirred at 0° C. 2(R)-tert-butoxycarbonylamino-3-triphenylmethylthiopropanal (prepared as described in Example 1C in WO 95/00497) is added and the mixture is stirred at 25° C. for from 2 to 100 hrs. The solution is evaporated to dryness and the residue is take up in dichloromethane and washed with saturated aqueous sodium bicarbonate and then brine. The dichloromethane layer is dried over magnesium sulfate and the solution is filtered and evaporated to dryness to give the product compound. The latter is purified on a silica gel column using 0.5%–1% (10% concentrated ammonium hydroxide in methanol)-dichloromethane to give the product compound.

The product compound from Step D above is dissolved in dichloromethane containing trifluororacetic acid. Triethylsilane is added and the mixture stirred at 25° C. for 1 hr. The reaction is worked up and chromatographed as described in Example 1E (WO 95/00497), the product being isolated as the hydrochloride salt.

EXAMPLE 2

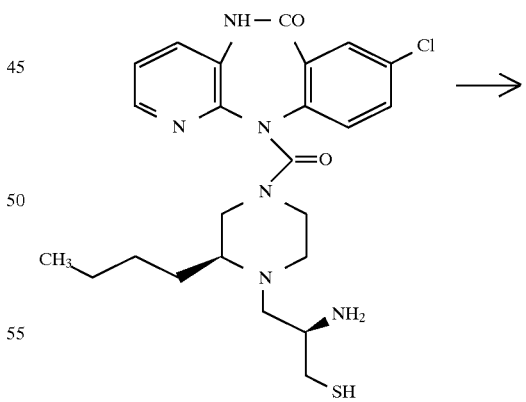

EXAMPLES 3–7

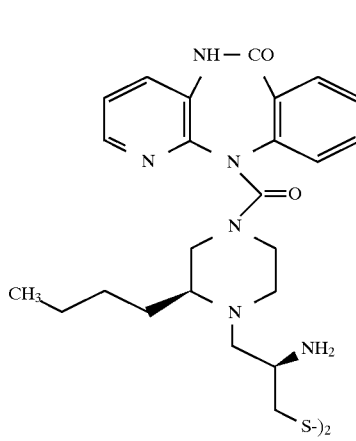

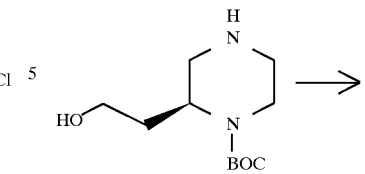

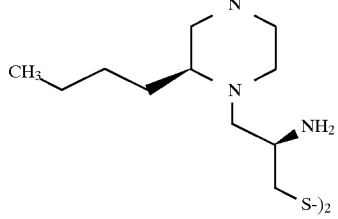

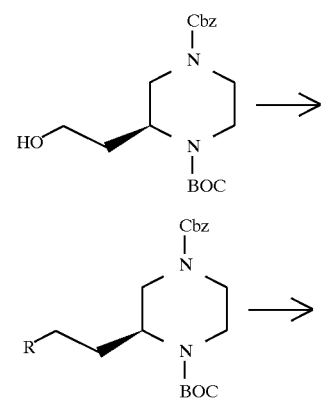

The product compound from Example 1E above as the free base is dissolved in methanol containing iodine and stirred at 25° C. for 30 mins. The solution is evaporated to dryness and the residue is taken up in dichloromethane and washed in saturated aqueous sodium bicarbonate and then brine. The dichloromethane layer is dried over magnesium sulfate filtered and evaporated to dryness to give the product compound. The product compound is purified on a silica gel column using 3% (10% concentrated ammonium hydroxide in methanol)-dichloromethane to give the product compound.

The product compound from Example 13A (WO 95/00497) is reacted with benzyloxycarbonyl chloride under standard conditions known to one skilled in the art, to give the N-Cbz protected alcohol shown above. After purification in the usual way the latter may be reacted with a variety of reagents shown in Column 1 of Table 1 to give the corresponding N-Cbz protected intermediates where R is as defined in Column 2 of Table 1. After purification in the usual way the latter may be deprotected using mild catalytic hydrogenation procedures known in the art, to give after suitable purification, the final desired intermediates shown in Column 2 of Table 1.

TABLE 1

| Column 1 | Column 2 |
|---|---|
|  and NaH | R = 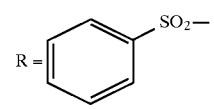 |
| | Prepared as described in Example 14A(WO95/00497) |
| | Example 3. |
| $C_6H_5SSC_6H_5$ + $(n\text{-}Bu)_3P$ | R = (phenyl-SO$_2$—) |
| | Prepared as described in Example 20B and 20C (WO95/00497) |
| | Example 4. |

TABLE 1-continued

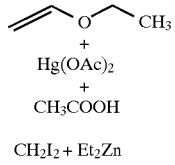

EXAMPLE 8

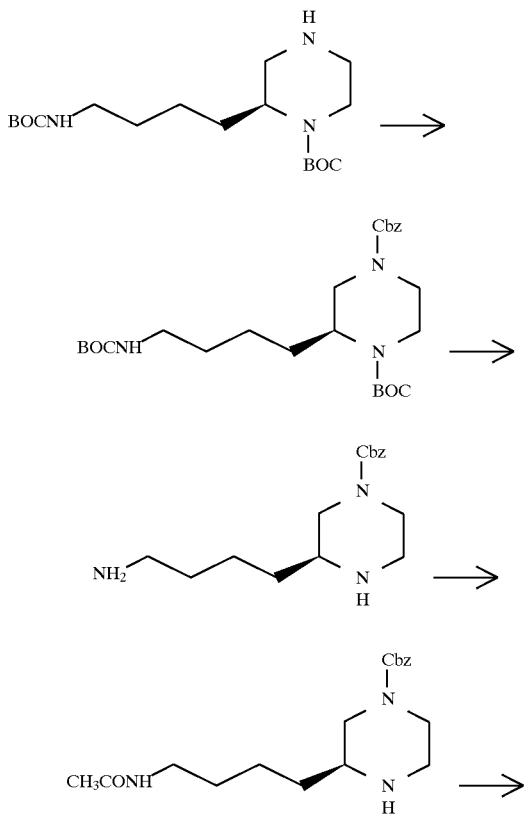

The product compound from Example 27D (WO 95/00497) is converted by the scheme shown above, using standard procedures known to one skilled in the art, into 1-tert-butoxycarbonyl-2(S)-(4-acetylaminobutyl) piperazine.

EXAMPLES 9–18

By essentially the same procedures as set forth in Examples 1B–E above but using the compounds set forth in Column 1, Table 1 below in place of 1-tert-butoxycarbonyl-2(S)-n-butylpiperazine, one can obtain compounds of the formula:

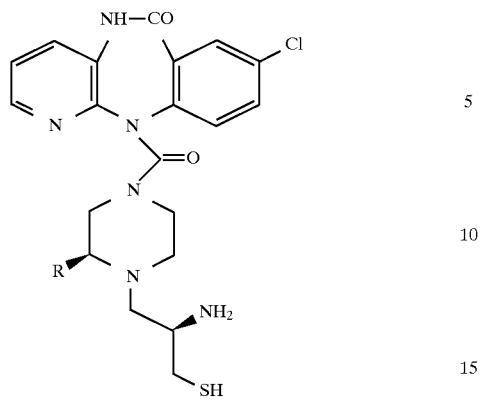

wherein R is as listed in Column 2, Table 2

TABLE 2

| Column 1 | Column 2 |
|---|---|
| ![structure with C₆H₅CH₂ and BOC] Prepared as described in Example 6C in WO 95/00497. | R = C₆H₅CH₂—<br>Example 9 |
| ![structure with CH₃OCH₂CH₂ and BOC] Prepared as described in Example 7D in WO 95/00497. | R = CH₃OCH₂CH₂—<br>Example 10 |
| ![structure with CH₃SCH₂CH₂ and BOC] Prepared as described in Example 8C in WO 95/00497. | R = CH₃SCH₂CH₂—<br>Example 11 |
| ![structure with CH₃O(CH₂)₃ and BOC] Prepared as described in Example 18D in WO 95/00497. | R = CH₃O(CH₂)₃—<br>Example 12 |

TABLE 2-continued

| Column 1 | Column 2 |
|---|---|
| 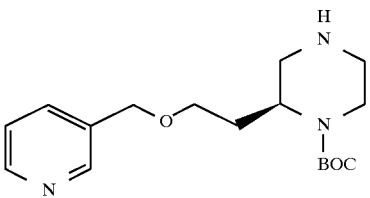<br>Prepared as described in Example 3 above | R = 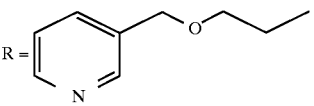<br>Example 13 |
| 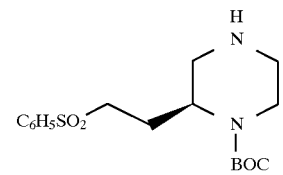<br>Prepared as described in Example 4 above | R = $C_6H_5SO_2$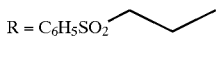<br>Example 14 |
| 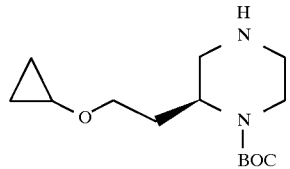<br>Prepared as described in Example 5 above | R = 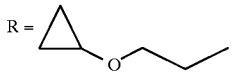<br>Example 15 |
| 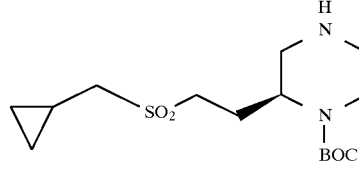<br>Prepared as described in Example 6 above | R = 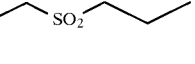<br>Example 16 |
| 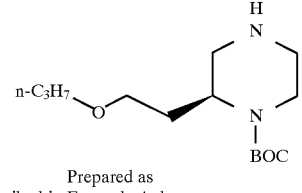<br>Prepared as described in Example 4 above | R = n-$C_3H_7O(CH_2)_2$—<br>Example 17 |
| 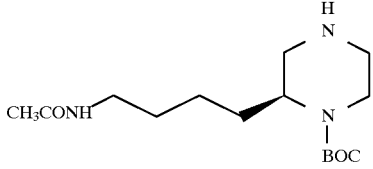<br>Prepared as described in Example 8 above | R = $CH_3CONH(CH_2)_4$—<br>Example 18 |

EXAMPLE 19

Prepation of:

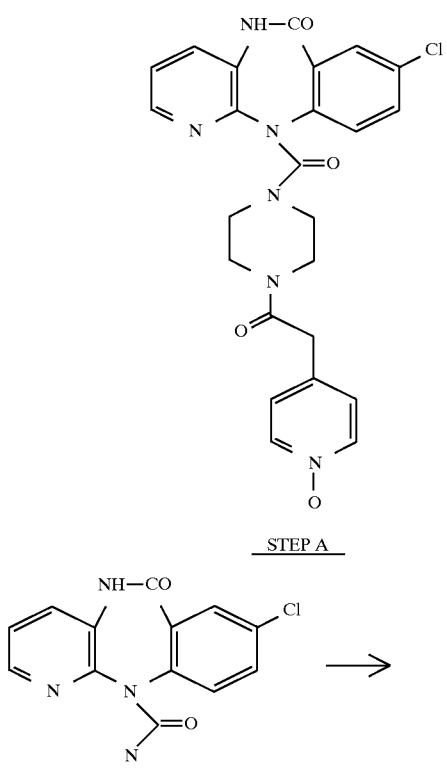

STEP A

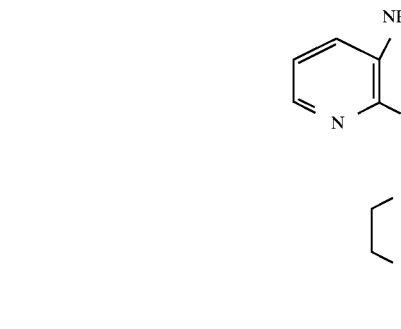 → 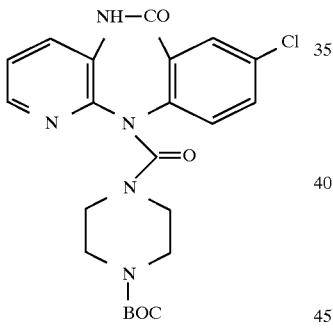

The product compound from Example 1A above is reacted with 1-N-tert-butoxycarbonylpiperazine as described in Example 1B above to afford the product compound.

STEP B

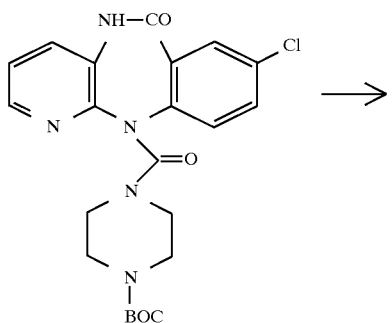 →

STEP B (continued)

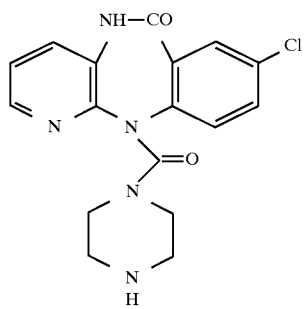

The product compound from Step A above is reacted as described in Example 1C to afford the product compound.

STEP C

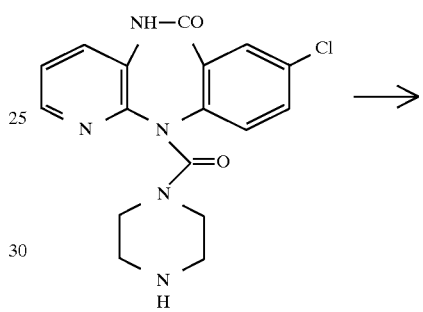 →

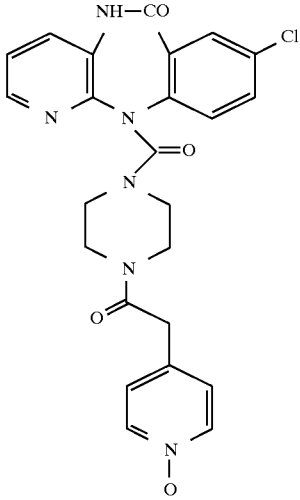

The product compound from Step B above is reacted with 4-pyridylacetic acid-1-N-oxide (prepared as described in Preparative Example 15 above), in the presence of DEC, HOBT and N-methylmorpholine in DMF as the solvent at 25° C. for 24 hours to give after purification the product compound.

EXAMPLES 20–23

By essentially the same procedure as described in Example 19 above and using in place of 4-pyridylacetic acid-1-N-oxide, the reagents in column 1, may be obtained the product compounds of Examples 20–23.

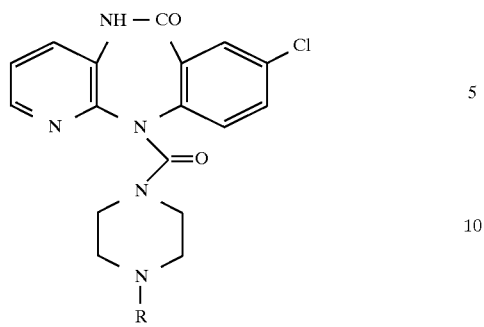
TABLE 3
| Column 1 | Column 2 |
|---|---|
| 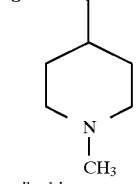<br>Prepared as descibed in<br>Preparative Example 9C above | R = 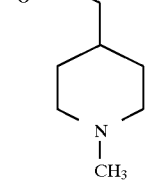<br>Example 20 |
| 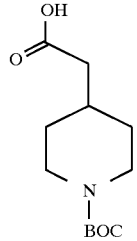<br>Prepared as descibed in<br>Preparative Example 9D above | R = 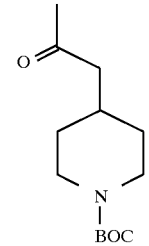<br>Example 21 |
| 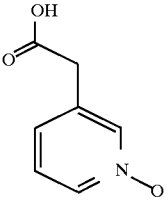<br>Prepared as descibed in<br>Preparative Example 1 above | R = 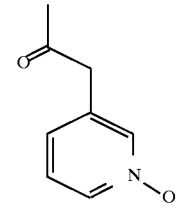<br>Example 22 |
| 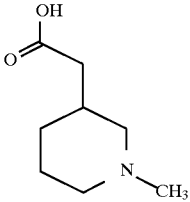<br>Prepared as descibed in<br>Preparative Example 10C above | R = 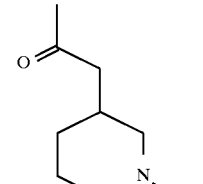<br>Example 23 |

TABLE 3-continued

| Column 1 | Column 2 |
|---|---|
| 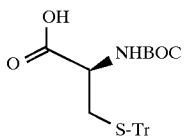<br>Reacted essentially as described in Example 19C above and deprotected as desribed in Example 1E above | 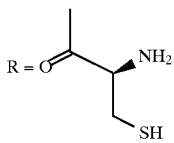<br>Example 24 |
| 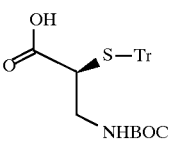<br>Prepared from iso-cysteine (L. M. Gustavson and A. Srinivasan, Synthetic Communications, 21(2), 265-270(1991), which is reacted essentially as described in Example 19C above and deprotected as described in Example 1E above | 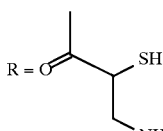<br>Example 25 |

EXAMPLE 26

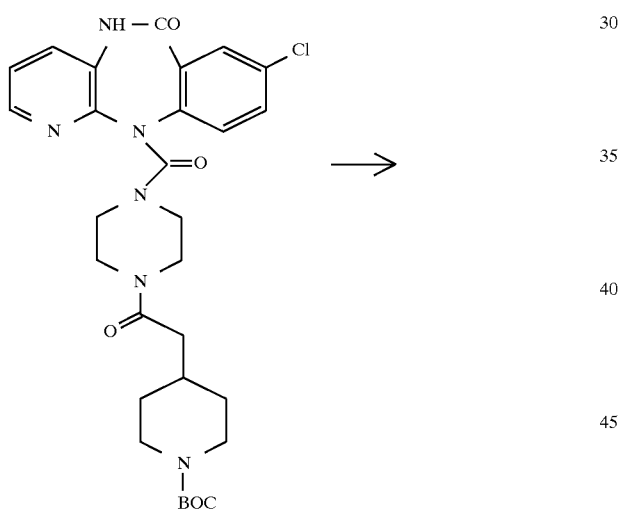 →

-continued

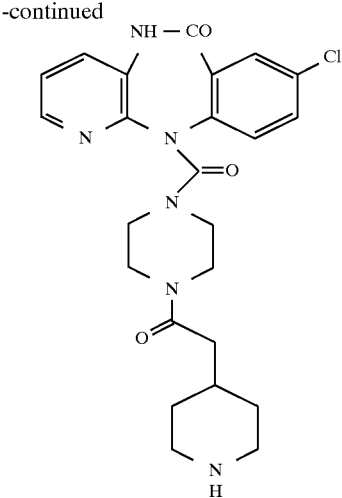

The product compound from Example 21 above is reacted as described in Example 1C above to give the product compound.

EXAMPLES 27–33

By using the reagents and procedures as outlined in Column 1, the product compound of Example 26 above may be converted into the product compounds shown in Column 2.

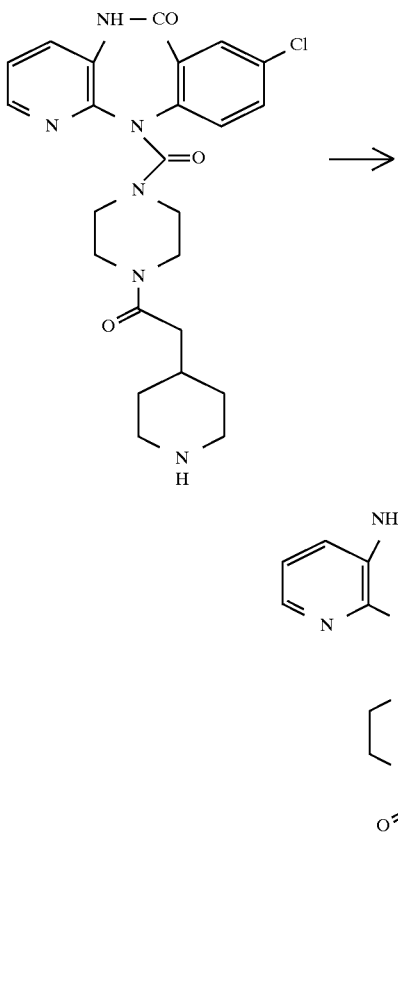

TABLE 4

| Column 1 | Column 2 |
|---|---|
| Ac$_2$O/CH$_3$OH | R = COCH$_3$ |
| | Example 27 |
| TMSNCO/CH$_2$Cl$_2$ | R = CONH$_2$ |
| | Example 28 |
| CH$_3$NCO/CH$_2$Cl$_2$ | R = CONHCH$_3$ |
| | Example 29 |
| CH$_3$NCS/CH$_2$Cl$_2$ | R = CSNHCH$_3$ |
| | Example 30 |
| BOCNH—CH(CH$_2$OH)—COOH | R = NH$_2$—CH(CH$_2$OH)—CO— |
| Reacted as described in Example 19C above and deprotected with acid as described in Example 1C above. | Example 31 |
| BOCNH—CH(CH$_2$S-Tr)—COOH | R = NH$_2$—CH(CH$_2$SH)—CO— |
| Reacted as described in Example 19C above and deprotected as described in Example 1E above. | Example 32 |
| BOCNH—CH(CH$_2$S—)$_2$—COOH | R = NH$_2$—CH(CH$_2$S—)$_2$—CO— |
| Reacted as described in Example 19C above and deprotected as described in Example 1C above. | Example 33 |

EXAMPLE 34

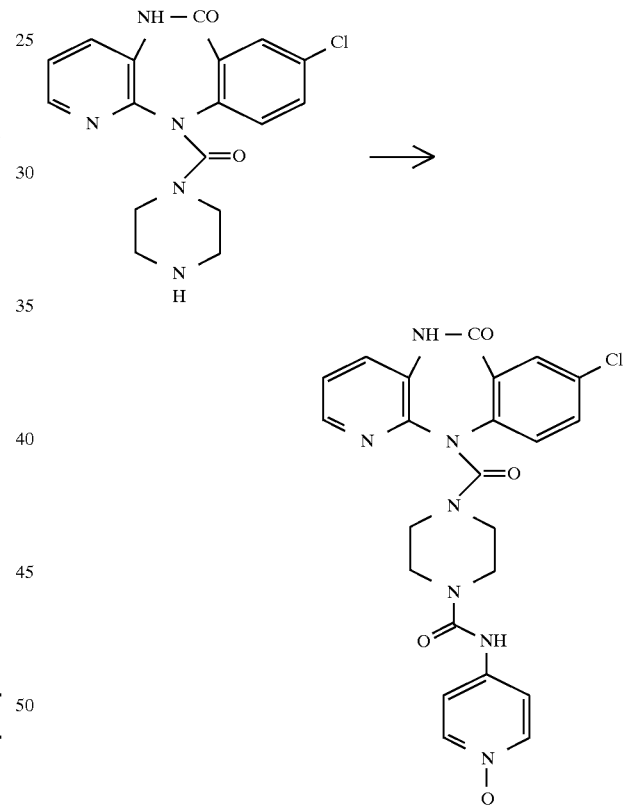

The product compound from Preparative Example 17 above is heated under reflux in anhydrous toluene at 110° C. for about 0.5 hours to give the isocyanate and then cooled to 25° C. The product compound from Example 19B above is added in anhydrous toluene to the solution of the isocyanate above and the mixture is stirred under argon at 25° C. for 112 hours to give, after the usual purification, the product compound.

Alternatively the product compound may be prepared by fusing the product compound from Preparative Example 17 with the carbamate,

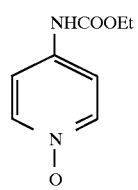

at 160° C. for 3 hours to afford, after purification the product compound.

EXAMPLE 35

Preparation of:

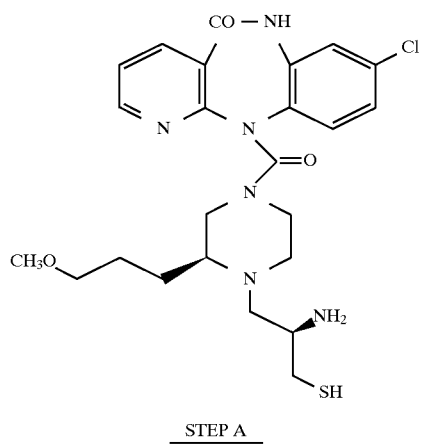

STEP A

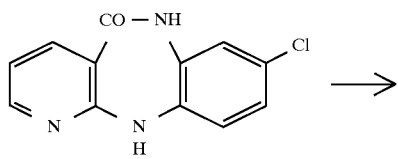

The product starting material is prepared as described in C. Hoffman and A. Faure, Bull. Soc. Chim. France, 1966 (7), 2316–2319, and is reacted by the process described in Example 1A above to give the product compound which is used without further purification.

STEP B

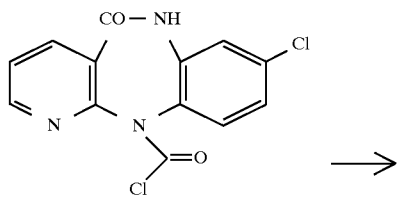

-continued
STEP B

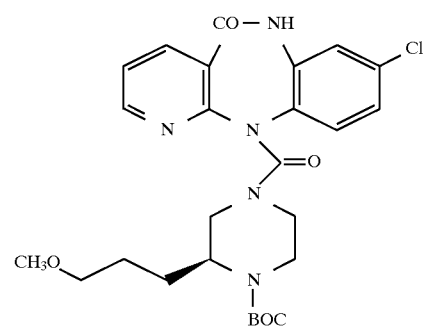

The product compound from Step A above is reacted with 1-tert-butoxycarbonyl-2(S)-(3-methoxy-1-propyl)-piperazine prepared as described in Example 18D (WO 95/00497).

STEP C

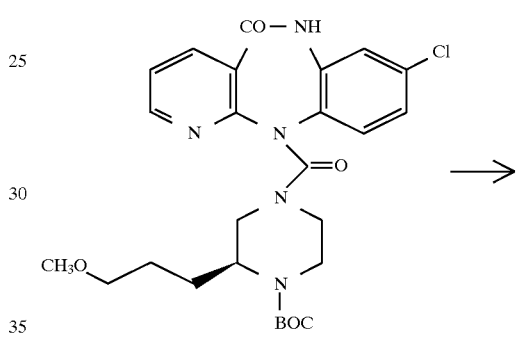

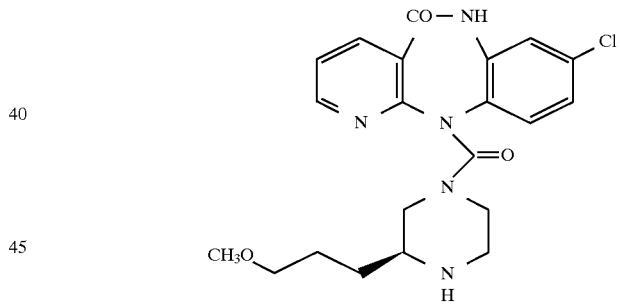

The product compound from Step B above is reacted as described in Example 1C above to give the product compound.

STEP D

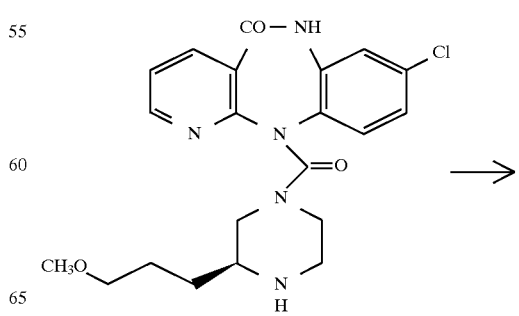

STEP D

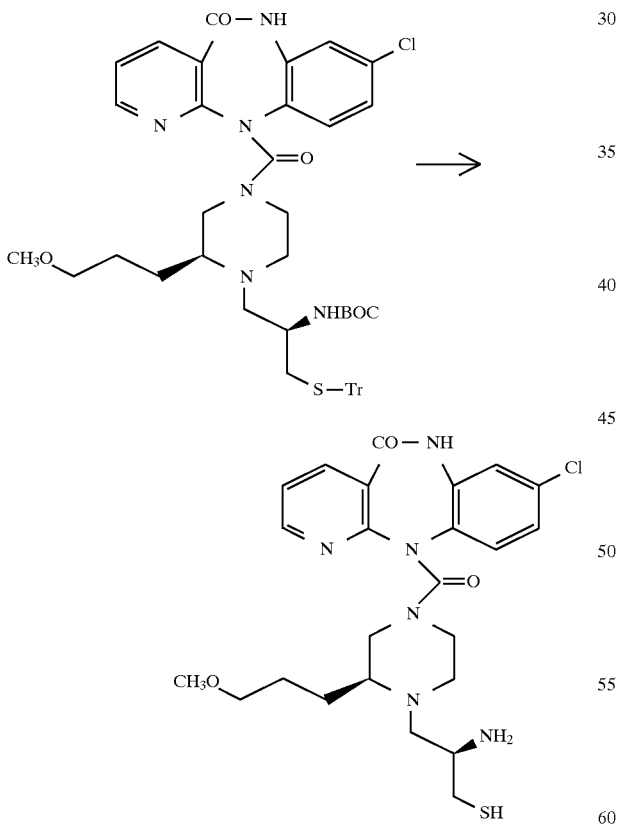

The product compound from Step C above is reacted as described in Example 1D above to give the product compound.

STEP E

The product compound from Step D above is reacted as described in Example 1E above to give the product compound which is purified in the usual way.

EXAMPLE 36

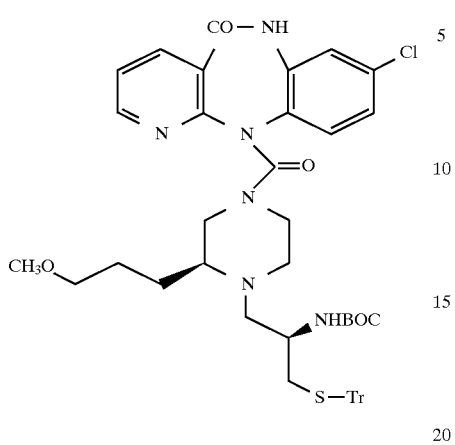

The product compound from Example 35C above is reacted with the product compound from Preparative Example 20 in a 1.1. mixture of pyridine and dichloromethane at 25° C. for 19 hours to give, after purification, the product compound.

EXAMPLE 37

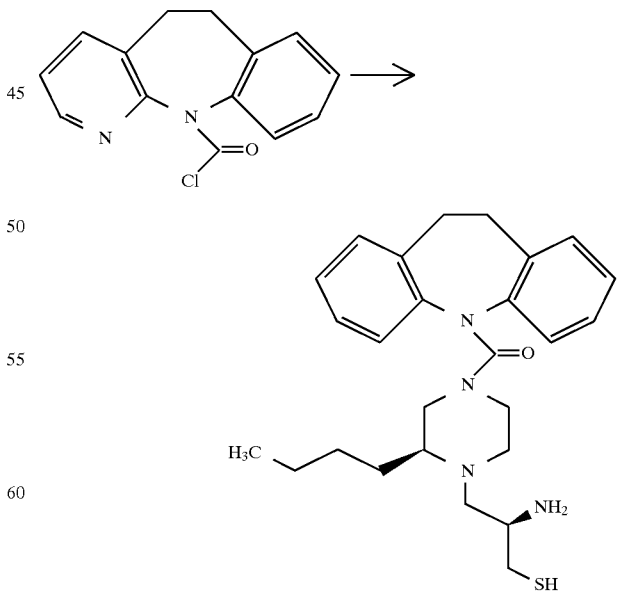

By substituting iminodibenzyl-5-carbonyl chloride for the starting material of Example 1B above and using essentially the same methods as described in Examples 1B–E above, the product compound may be prepared.

EXAMPLE 38

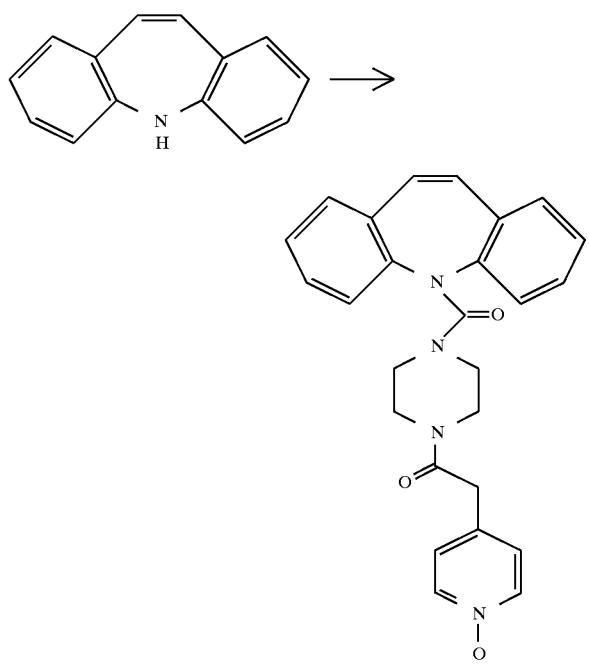

By substituting iminostilbene for the starting material of Example 1A above and using essentially the same methods as described in Examples 1A–E above, the product compound may be prepared.

EXAMPLE 39

Preparation of:

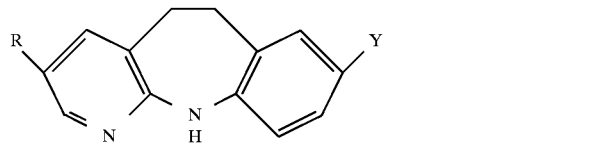

The product compounds may be prepared by the following reaction scheme:

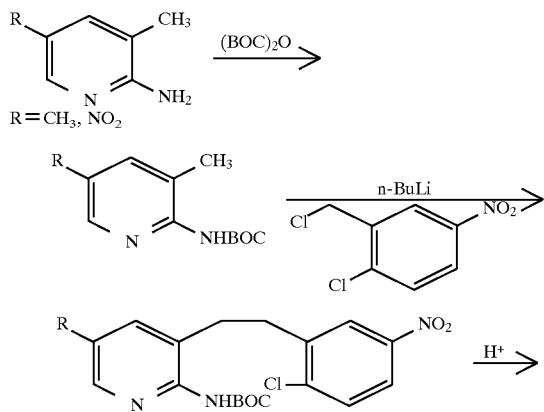

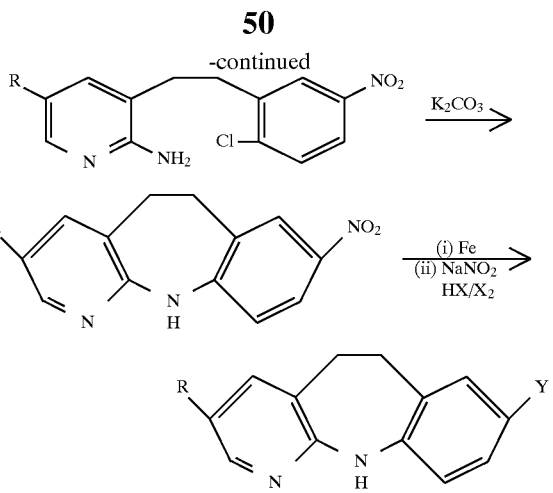

Y=Cl, Br may be prepared from the interediate $NH_2$-compound. Where $R=NO_2$ the latter may be reduced as above to give the amino compound which may in turn be diazotized and converted into the chloro or bromo derivative.

EXAMPLE 40

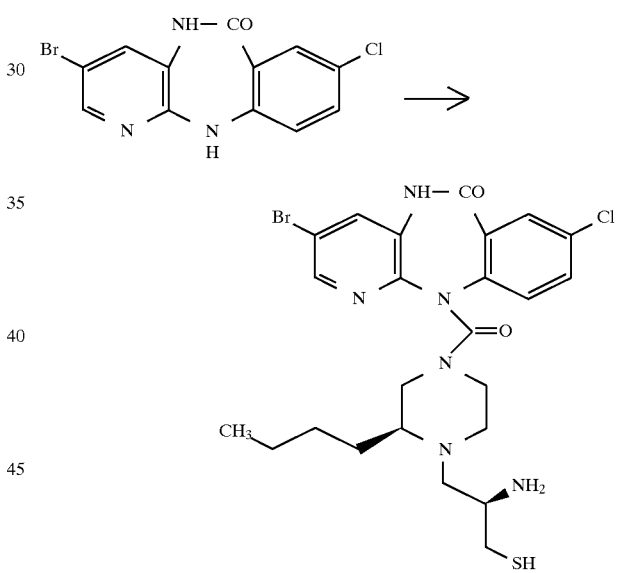

The product reactant may be prepared by the methods described in Example 39 above and reacted essentially as described in Examples 1A–E above to give the product compound.

EXAMPLE 41

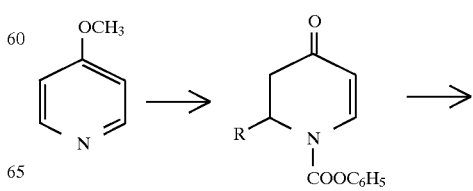

51

-continued

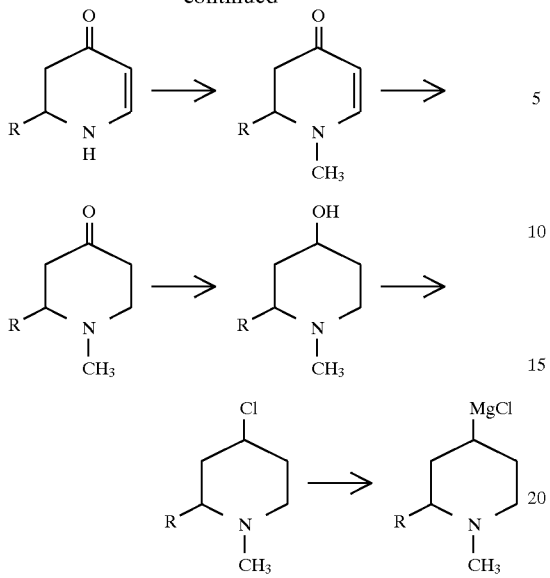

The product substituted piperidines may be prepared by essentially the same methods as described in D. L. Comins and J. D. Brown, Tetrahedron Letters, vol. 27 No. 38, pgs. 4549–4552, 1986. Thus, 4-methoxypyridine may be converted using a variety of alkyl Grignard reagents (wherein R is as illustrated below) and phenylchloroformate to the desired unsaturated ketopiperidines. Removal of the phenylcarbamoyl group with either base or acid followed by alkylation with a suitable alkyl iodide such as methyl iodide in the presence of sodium hydride gives the n-alkyl-piperidines. Reduction of the double bond under standard conditions known in the art affords the saturated ketopiperidine which on reduction with sodium borohydride affords the 4-hydroxypiperidine. The latter is reacted with a suitable chlorinating agent such as thionyl chloride to afford the 4-chloro piperidine which may in turn be converted by reaction with magnesium into the product compounds.

$R = CH_3(CH_2)_3 —$,

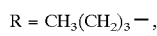
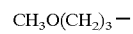
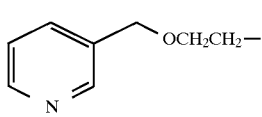
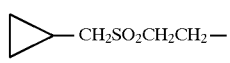

52

EXAMPLE 42

Preparation of:

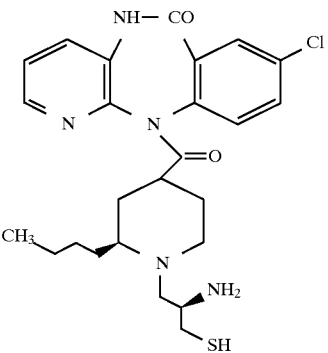

STEP A

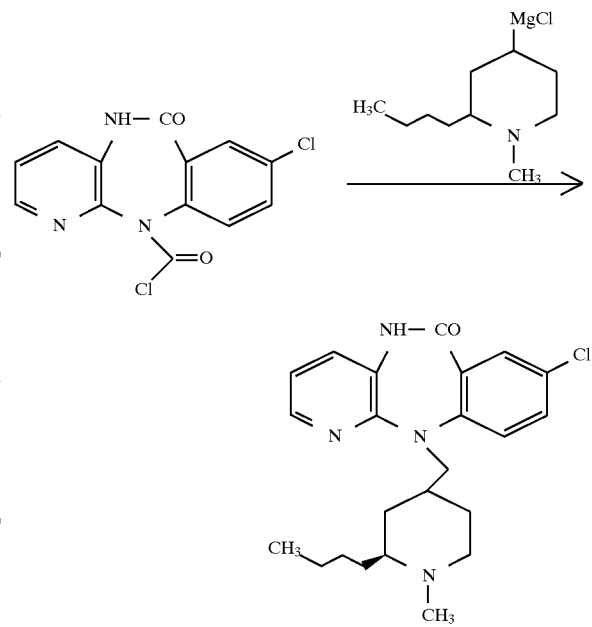

The product compound from Step A above is reacted with the piperidine Grignard reagent shown above (prepared as described in Example 41 above) to give the product compound.

STEP B

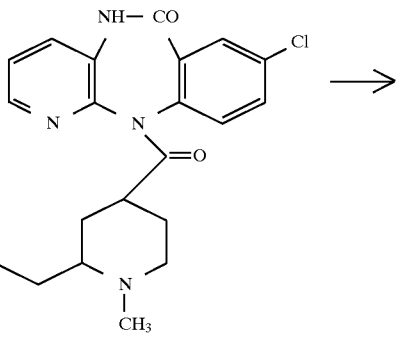

STEP B

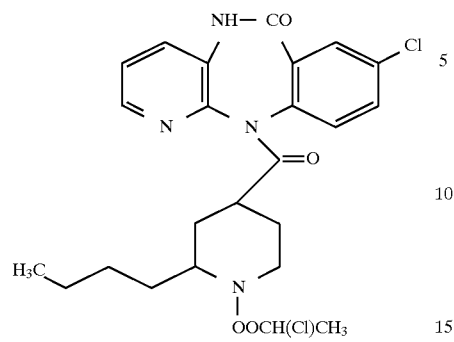

The product compound from Step A above is reacted with α-chloroethylchloroformate (as described in: R. A. Olofson, et. al., J. Org. Chem., 49(11), 2081–2082 (1984)) to afford the product compound.

STEP C

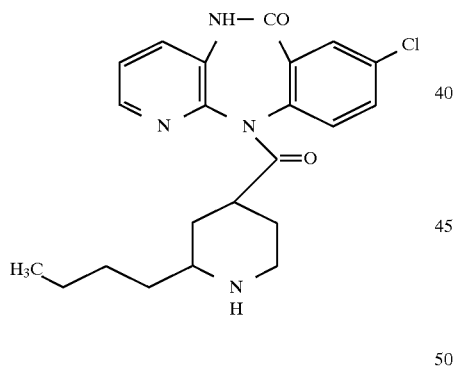

The product compound from Step B above is refluxed in methanol (as described in: R. A. Olofson, et. al., J. Org. Chem., 49(11), 2081–2082 (1984)) to give the mono hydrochloride salt of the product compound. The latter is converted into the free base in the usual manner to give the product compound.

STEP D:

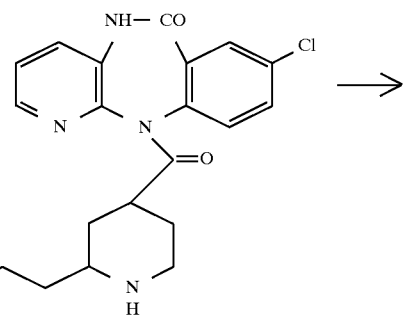

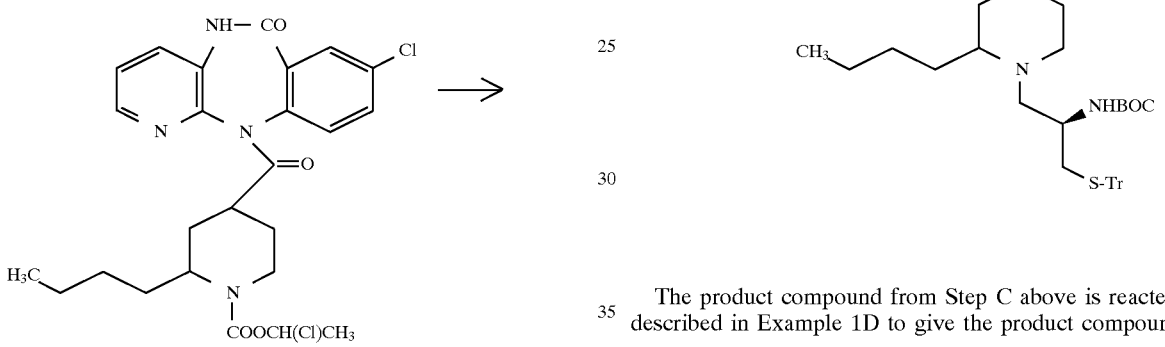

The product compound from Step C above is reacted as described in Example 1D to give the product compound.

STEP E

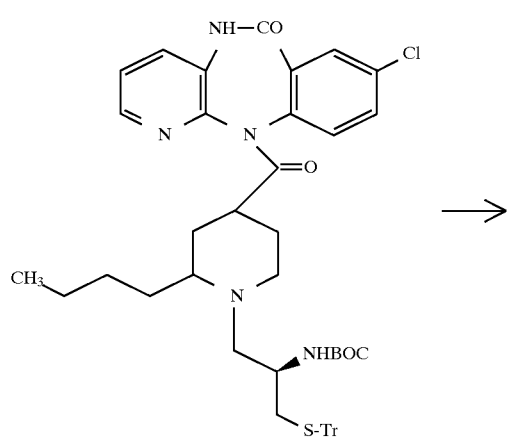

-continued
STEP E

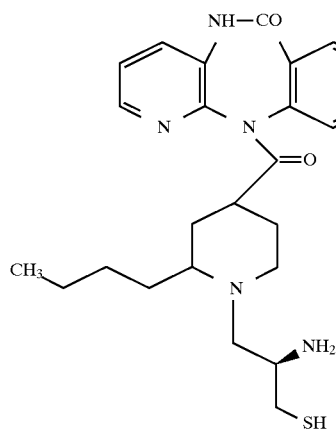

The product compound from Step D above is reacted as described in Example 1E to give the product compound.

EXAMPLE 43

Preparation of:

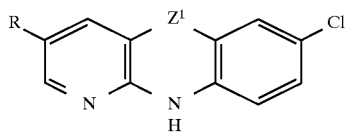

Wherein $Z^1$ is —NH—CO— or —CO—NH—.

One may obtain the product compounds by the procedures described in: W. E. Engel, et al., J. Med. Chem., 1989, 32, 1718–1724, and Hargrave et al. J. Med. Chem. 1991, 34, 2231–2241

The latter may be further manipulated for example where $R^3$ or $R^4$ are $NO_2$ into the compounds where $R^3$ or $R^4$ are $NH_2$, Cl, or Br, by similiar methods analogous to those described in steps A, B, C, D, and E below.

Step A

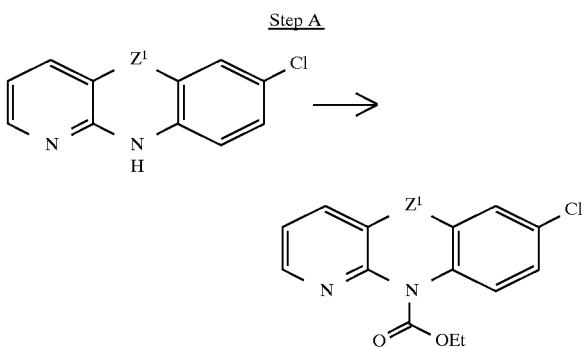

The starting compound is converted into the ethyl carbamate, or any suitable protecting group, by standard methods known in the art.

Step B

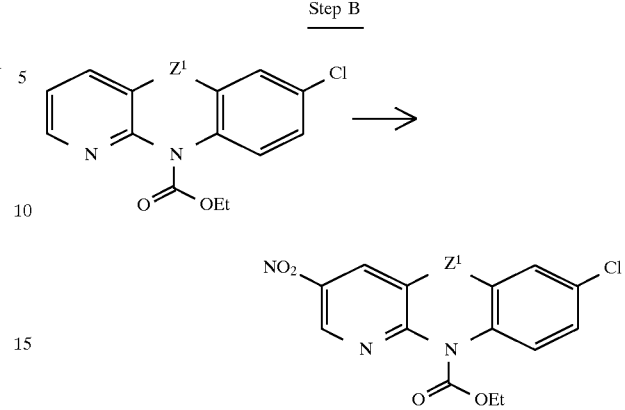

The product compound from step A is reacted with tetra-n-butylammonium nitrate in dichloromethane with TFAA at 0° C. for 3 hours and at 25° overnight, to give the title compound.

Step C:

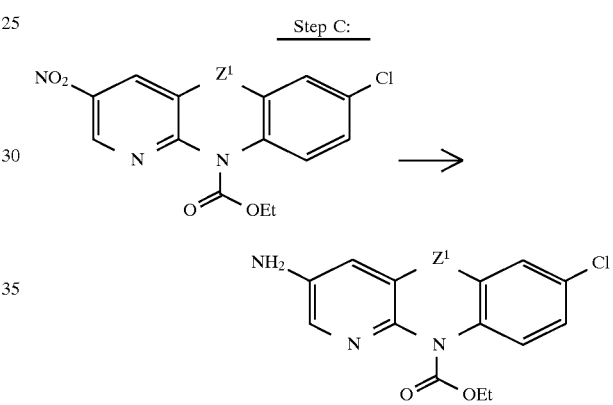

The Product of Step B in 85% EtOH (aqueous), is reduced with Fe filings and $CaCl_2$, at reflux for 16 hours, to give the product compound.

Step D:

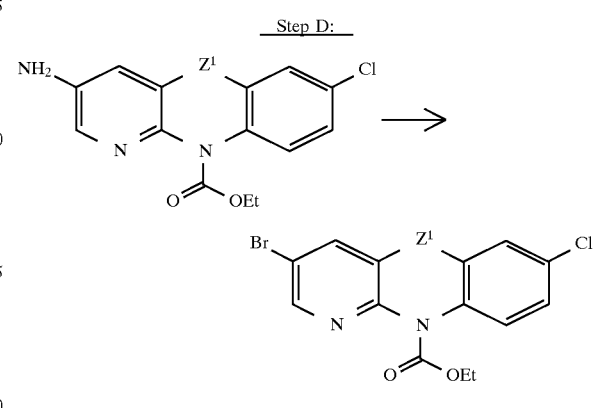

The Product of Step C in 48% HBr, is cooled to −5° C. Stir the mixture at −5° C. for 15 minutes and slowly add a solution of $NaNO_2$ in water. Stir for 45 minutes, then quench with 50% NaOH (aqueous) to pH~10. Extract with EtOAc, dry the combined extracts over $MgSO_4$ and concentrate in vacuo to give the product compound.

Step E:

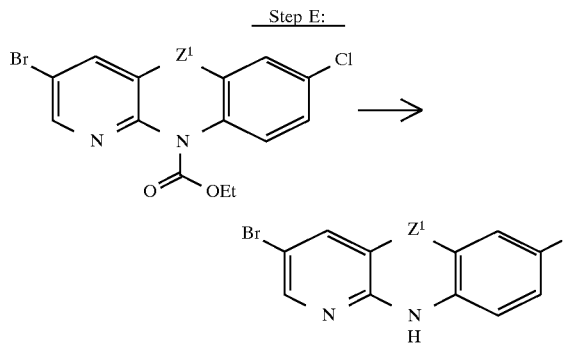

Hydrolyze the Product of Step D via methods known in the art to give the product compound.

EXAMPLE 44

Starting materials for compounds of formula 1.0 wherein Z is —CH=CH— may be prepared by the following reaction sequence:

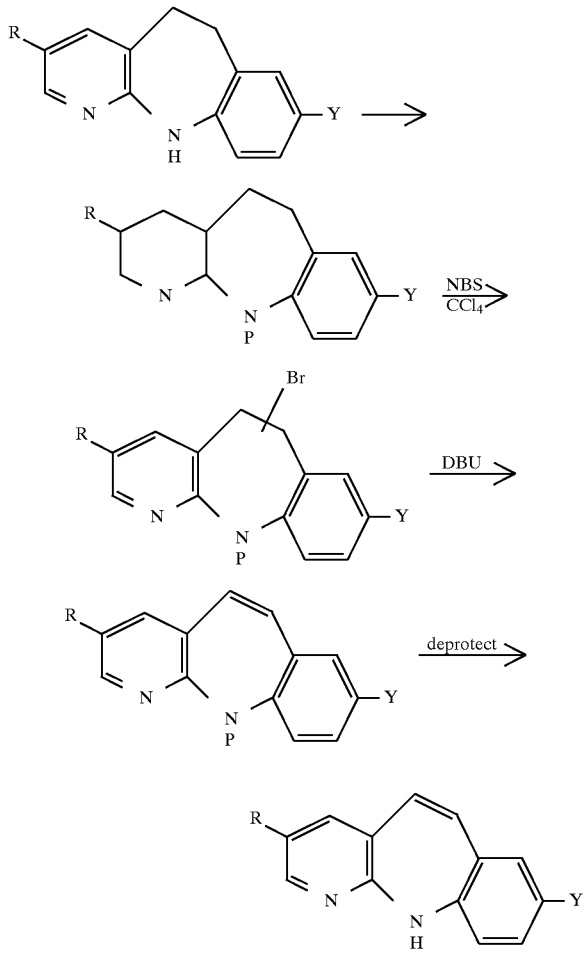

Wherein P is a protecting group such as BOC.

EXAMPLE 45

To produce a compound of formula 1.0 wherein Z is —CO—NR$^{16}$— or —NR$^{16}$—CO— wherein R$^{16}$ is other than H, the tricyclic starting compound e.g.:

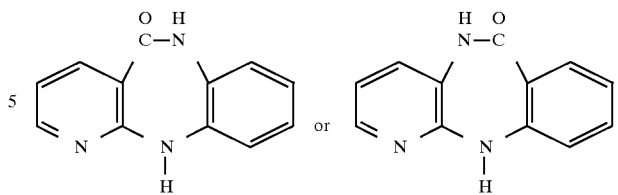

is substituted by the procedure of Hargrave et al. J. Med. Chem., 1991, 34, 2231–2241 using a suitable alkyl halide e.g. methyl iodide and sodium hydride in DMF as the solvent.

ASSAYS

The utility of the compounds of the present invention can be demonstrated by the following assay procedures.

1. In vitro enzyme assays: Inhibition of farnesyl protein transferase and geranylgeranyl protein transferase.

Both farnesyl protein transferase (FPT) and geranylgeranyl protein transferase (GGPT) I are partially purified from rat brain by ammonium sulfate fractionation followed by Q-Sepharose (Pharmacia, Inc.) anion exchange chromatography essentially as described by Yokoyama et al (Yokoyama, K., et al., (1991), A protein geranylgeranyltransferase from bovine brain: Implications for protein prenylation specificity, *Proc. Natl. Acad. Sci USA* 88: 5302–5306, the disclosure of which is incorporated herein by reference thereto). Human farnesyl protein transferase is also expressed in *E. coli*, using cDNA clones encoding both the α and β subunits. The methods used are similar to those published (Omer, C. et al., (1993), Characterization of recombinant human farnesyl protein transferase: Cloning, expression, farnesyl diphosphate binding, and functional homology with yeast prenyl-protein transferases, Biochemistry 32:5167–5176). Human farnesyl protein transferase is partially-purified from the soluble protein fraction of *E. coli* as described above. The tricyclic farnesyl protein transferase inhibitors disclosed herein inhibit both human and rat enzyme with similar potencies. Two forms of val$^{12}$-Ha-Ras protein are prepared as substrates for these enzymes, differing in their carboxy terminal sequence. One form terminates in cysteine-valine-leucine-serine (Ras-CVLS) the other in cystein-valine-leucine-leucine (Ras-CVLL). Ras-CVLS is a substrate for the farnesyl protein transferase while Ras-CVLL is a substrate for geranylgeranyl protein transferase I. The cDNAs encoding these proteins are constructed so that the proteins contain an amino-terminal extension of 6 histidine residues. Both proteins are expressed in *Escherichia coli* and purified using metal chelate affinity chromatography. The radiolabelled isoprenyl pyrophosphate substrates, [$^3$H]farnesyl pyrophosphate and [$^3$H]geranylgeranyl pyrophosphate, are purchased from a commercial source, such as DuPont/New England Nuclear.

Several methods for measuring farnesyl protein transferase activity are known (Reiss et al 1990, *Cell* 62: 81; Schaber et al 1990, *J. Biol. Chem.* 265: 14701; Manne et al 1990, *PNAS* 87: 7541; and Barbacid & Manne 1993, U.S. Pat. No. 5,185,248). The activity is assayed by measuring the transfer of [$^3$H]farnesyl from [$^3$H]farnesyl pyrophosphate to Ras-CVLS using conditions similar to those described by Reiss et al., 1990 (*Cell* 62: 81) The reaction mixture contains 40 mM Hepes, pH 7.5; 20 mM magnesium chloride; 5 mM dithiothreitol; 0.25 μM [$^3$H]farnesyl pyrophosphate; 10 μl Q-Sepharose-purified farnesyl protein transferase; the indicated concentration of tricyclic compound or dimethylsulfoxide (DMSO) vehicle control (5% DMSO final); and 5 μM Ras-CVLS in a total volume of 100

μl. The reaction is allowed to proceed for 30 minutes at room temperature and then stopped with 0.5 ml of 4% sodium dodecyl sulfate (SDS) followed by 0.5 ml of cold 30% trichloracetic acid (TCA). Samples are allowed to sit on ice for 45 minutes and precipitated Ras protein is then collected on GF/C filter paper mats using a Brandel cell harvester. Filter mats are washed once with 6% TCA, 2% SDS and radioactivity is measured in a Wallac 1204 Betaplate BS liquid scintillation counter. Percent inhibition is calculated relative to the DMSO vehicle control.

The geranylgeranyl protein transferase I assay is essentially identical to the farnesyl protein transferase assay described above, with two exceptions: [$^3$H] geranylgeranylpyrophosphate replaces farnesyl pyrophosphate as the isoprenoid donor and Ras-CVLL is the protein acceptor. This is similar to the assay reported by Casey et al (Casey, P. J., et al., (1991), Enzymatic modification of proteins with a geranylgeranyl isoprenoid, *Proc. Natl. Acad. Sci, USA* 88: 8631–8635, the disclosure of which is incorporated herein by reference).

2. Cell-Based Assay: Transient expression of val$^{12}$-Ha-Ras-CVLS and val$^{12}$-Ha-Ras-CVLL in COS monkey kidney cells: Effect of farnesyl protein transferase inhibitors on Ras processing and on disordered cell growth induced by transforming Ras.

COS monkey kidney cells are transfected by electroporation with the plasmid pSV-SPORT (Gibco/BRL) containing a cDNA insert encoding either Ras-CVLS or Ras-CVLL, leading to transient overexpression of a Ras substrate for either farnesyl protein transferase or geranylgeranyl protein transferase I, respectively (see above).

Following electroporation, cells are plated into 6-well tissue culture dishes containing 1.5 ml of Dulbecco's-modified Eagle's media (GIBCO, Inc.) supplemented with 10% fetal calf serum and the appropriate farnesyl protein transferase inhibitors. After 24 hours, media is removed and fresh media containing the appropriate drugs is re-added.

48 hours after electroporation cells are examined under the microscope to monitor disordered cell growth induced by transforming Ras. Cells expressing transforming Ras become more rounded and refractile and overgrow the monolayer, reminiscent of the transformed phenotype. Cells are then photographed, washed twice with 1 ml of cold phosphate-buffered saline (PBS) and removed from the dish by scraping with a rubber policeman into 1 ml of a buffer containing 25 mM Tris, pH 8.0; 1 mM ethylenediamine tetraacetic acid; 1 mM phenylmethylsulfonyl fluoride; 50 μM leupeptin; and 0.1 μM pepstatin. Cells are lysed by homogenization and cell debris is removed by centrifugation at 2000×g for 10 min.

Cellular protein is precipitated by addition of ice-cold trichloroacetic acid and redissolved in 100 μl of SDS-electrophoresis sample buffer. Samples (5–10 μl) are loaded onto 14% polyacrylamide minigels (Novex, Inc.) and electrophoresed until the tracking dye neared the bottom of the gel. Proteins resolved on the gels are electroblotted onto nitrocellulose membranes for immunodetection.

Membranes are blocked by incubation overnight at 4° C. in PBS containing 2.5% dried milk and 0.5% Tween-20 and then incubated with a Ras-specific monoclonal antibody, Y13-259 (Furth, M. E., et al., (1982), Monoclonal antibodies to the p21 products of the transforming gene of Harvey murine sarcoma virus and of the cellular ras gene family, *J. Virol.* 43: 294–304), in PBS containing 1% fetal calf serum for one hour at room temperature. After washing, membranes are incubated for one hour at room temperature with a 1:5000 dilution of secondary antibody, rabbit anti-rat IgG conjugated to horseradish peroxidase, in PBS containing 1% fetal calf serum. The presence of processed and unprocessed Ras-CVLS or Ras-CVLL is detected using a colorimetric peroxidase reagent (4-chloro-1-naphthol) as described by the manufacturer (Bio-Rad).

3. Cell Mat Assay:

Normal human HEPM fibroblasts are planted in 3.5 cm dishes at a density of 5×10$^4$ cells/dish in 2 ml growth medium, and incubated for 3–5 d to achieve confluence. Medium is aspirated from each dish and the indicator tumor cells, T24-BAG4 human bladder carcinoma cells expressing an activated H-ras gene, are planted on top of the fibroblast monolayer at a density of 2×10$^3$ cells/dish in 2 ml growth medium, and allowed to attach overnight. Compound-induced colony inhibition is assayed by addition of serial dilutions of compound directly to the growth medium 24 h after tumor cell planting, and incubating cells for an additional 14 d to allow colony formation. Assays are terminated by rinsing monolayers twice with phosphate-buffered saline (PBS), fixing the monolayers with a 1% glutaraldehyde solution in PBS, then visualizing tumor cells by staining with X-Gal (Price, J., et al., Lineage analysis in the vertebrate nervous system by retrovirus-mediated gene transfer, Proc. Natl. Acad. Sci.84, 156–160(1987)). In the colony inhibition assay, compounds are evaluated on the basis of two IC$_{50}$ values: the concentration of drug required to prevent the increase in tumor cell number by 50% (tIC$_{50}$) and the concentration of drug required to reduce the density of cells comprising the cell mat by 50% (mIC$_{50}$). Both IC$_{50}$ values are obtained by determining the density of tumor cells and mat cells by visual inspection and enumeration of cells per colony and the number of colonies under the microscope. The therapeutic index of the compound is quantitatively expressed as the ratio of mIC$_{50}$/tIC$_{50}$, with values greater than one indicative of tumor target specificity.

For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 70 percent active ingredient. Suitable solid carriers are known in the art, e.g. magnesium carbonate, magnesium stearate, talc, sugar, lactose. Tablets, powders, cachets and capsules can be used as solid dosage forms suitable for oral administration.

For preparing suppositories, a low melting wax such as a mixture of fatty acid glycerides or cocoa butter is first melted, and the active ingredient is dispersed homogeneously therein as by stirring. The molten homogeneous mixture is then poured into convenient sized molds, allowed to cool and thereby solidify.

Liquid form preparations include solutions, suspensions and emulsions. As an example may be mentioned water or water-propylene glycol solutions for parenteral injection.

Liquid form preparations may also include solutions for intranasal administration.

Aerosol preparations suitable for inhalation may include solutions and solids in powder form, which may be in combination with a pharmaceutically acceptable carrier, such as an inert compressed gas.

Also included are solid form preparations which are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

Preferably the compound is administered orally.

Preferably, the pharmaceutical preparation is in unit dosage form. In such form, the preparation is subdivided into unit doses containing appropriate quantities of the active component, e.g., an effective amount to achieve the desired purpose.

The quantity of active compound in a unit dose of preparation may be varied or adjusted from about 0.1 mg to 1000 mg, more preferably from about 1 mg. to 300 mg, according to the particular application.

The actual dosage employed may be varied depending upon the requirements of the patient and the severity of the condition being treated. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day if desired.

The amount and frequency of administration of the compounds of the invention and the pharmaceutically acceptable salts thereof will be regulated according to the judgment of the attending clinician considering such factors as age, condition and size of the patient as well as severity of the symptoms being treated. A typical recommended dosage regimen is oral administration of from 10 mg to 2000 mg/day preferably 10 to 1000 mg/day, in two to four divided doses to block tumor growth. The compounds are non-toxic when administered within this dosage range.

The following are examples of pharmaceutical dosage forms which contain a compound of the invention. The scope of the invention in its pharmaceutical composition aspect is not to be limited by the examples provided.

Pharmaceutical Dosage Form Examples

EXAMPLE A

Tablets

| No. | Ingredients | mg/tablet | mg/tablet |
|---|---|---|---|
| 1. | Active compound | 100 | 500 |
| 2. | Lactose USP | 122 | 113 |
| 3. | Corn Starch, Food Grade, as a 10% paste in Purified Water | 30 | 40 |
| 4. | Corn Starch, Food Grade | 45 | 40 |
| 5. | Magnesium Stearate | 3 | 7 |
| | Total | 300 | 700 |

Method of Manufacture

Mix Item Nos. 1 and 2 in a suitable mixer for 10–15 minutes. Granulate the mixture with Item No. 3. Mill the damp granules through a coarse screen (e.g., ¼", 0.63 cm) if necessary. Dry the damp granules. Screen the dried granules if necessary and mix with Item No. 4 and mix for 10–15 minutes. Add Item No. 5 and mix for 1–3 minutes. Compress the mixture to appropriate size and weigh on a suitable tablet machine.

EXAMPLE B

Capsules

| No. | Ingredient | mg/capsule | mg/capsule |
|---|---|---|---|
| 1. | Active compound | 100 | 500 |
| 2. | Lactose USP | 106 | 123 |
| 3. | Corn Starch, Food Grade | 40 | 70 |
| 4. | Magnesium Stearate NF | 7 | 7 |
| | Total | 253 | 700 |

Method of Manufacture

Mix Item Nos. 1, 2 and 3 in a suitable blender for 10–15 minutes. Add Item No. 4 and mix for 1–3 minutes. Fill the mixture into suitable two-piece hard gelatin capsules on a suitable encapsulating machine.

While the present invention has been described in conjunction with the specific embodiments set forth above, many alternatives, modifications and variations thereof will be apparent to those of ordinary skill in the art. All such alternatives, modifications and variations are intended to fall within the spirit and scope of the present invention.

What is claimed is:

1. A compound of the formula:

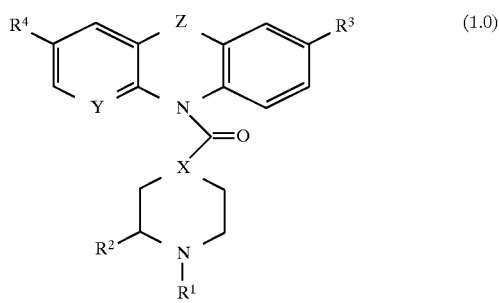

(1.0)

or a pharmaceutically acceptable salt thereof, wherein:

(1) $R^1$ is a group selected from:

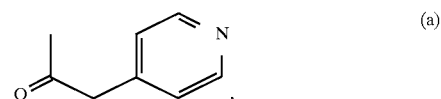

(a)

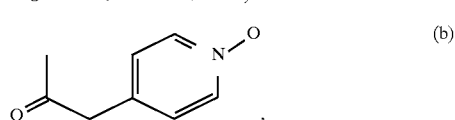

(b)

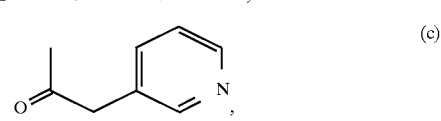

(c)

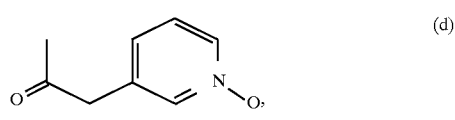

(d)

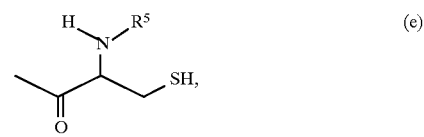

(e)

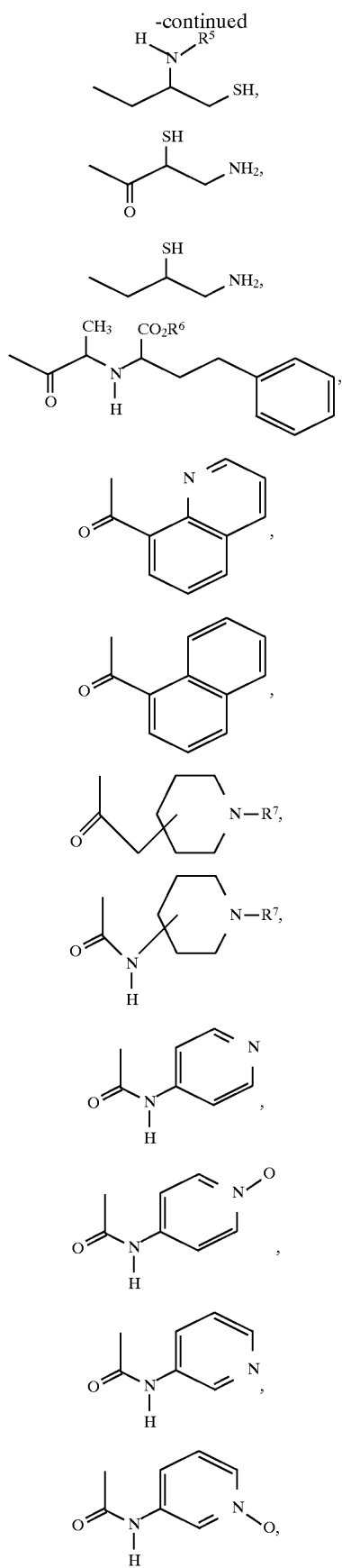
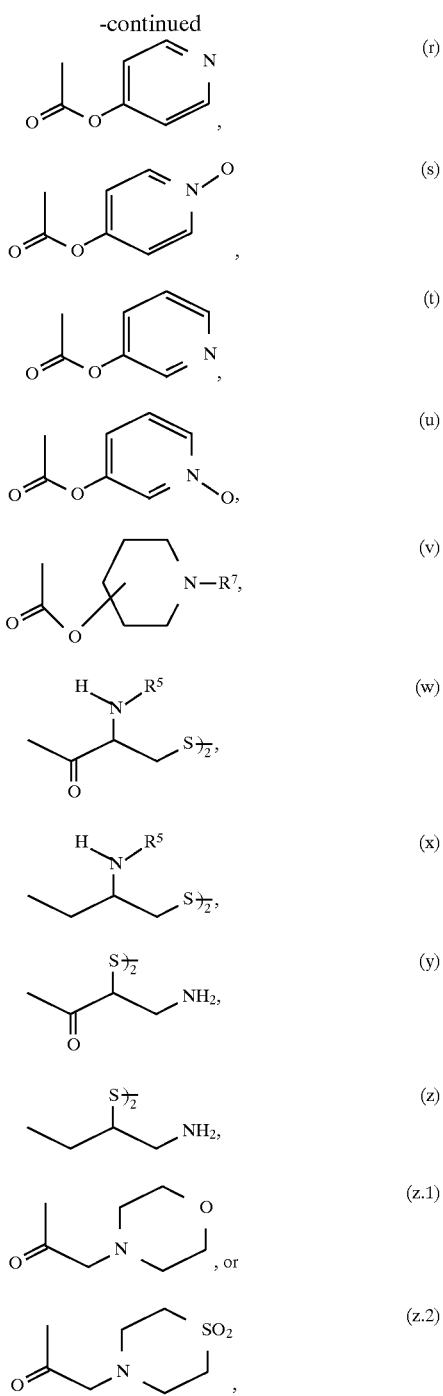
$R^2$ is selected from:
 (1) H,
 (2) $C_1$ to $C_8$ alkyl,
 (3) $C_2$ to $C_8$ alkenyl,
 (4) $C_2$ to $C_8$ alkynyl,
 (5)
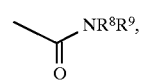
or (6)

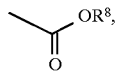

wherein said alkyl, alkenyl, or alkynyl is optionally substituted with one or more groups independently selected from:
(a) $C_6$ to $C_{15}$ aryl, aralkyl, heteroaryl wherein said heteroaryl is selected from the group consisting of triazolyl, 2-,3- or 4-pyridyl or pyridyl Noxide, or heterocycloalkyl wherein said heterocycloalkyl is selected from the group consisting of 2- or 3-tetrahydrofuranyl, 2- or 3-tetrahydrothienyl, 2-, 3- or 4-piperidinyl, 2- or 3-pyrolidinyl, 2- or 3-piperizinyl, and 2- or 4-dioxanyl; said aryl, aralkyl, heteroaryl or heterocycloalkyl optionally substituted with one or more:
  (1) $C_1$ to $C_4$ alkyl,
  (2) $(CH_2)_tOR^8$ wherein t is 1 to 4,
  (3) $(CH_2)_tNR^8R^9$ wherein t is 1 to 4,
  (4) halogen,
(b) $C_3$ to $C_6$ cycloalkyl,
(c) $-OR^8$,
(d) $-SR^8$,
(e) $-S(O)R^8$,
(f) $-SO_2R^8$,
(g) $-NR^8R^9$,
(h)

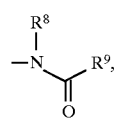

(i)

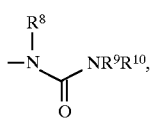

(j)

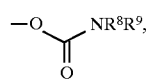

(k)

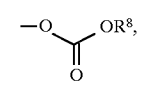

(l)

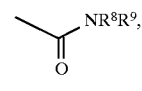

(m)
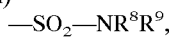

(n)

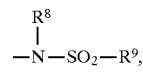

or (o)

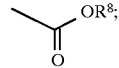

$R^3$ is selected from H, halogen or $C_1$ to $C_6$ alkyl;
$R^4$ is selected from H, halogen or $C_1$ to $C_6$ alkyl;
$R^5$ is selected from: H, $C_1$–$C_6$ alkyl,

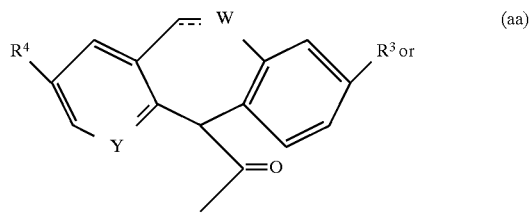

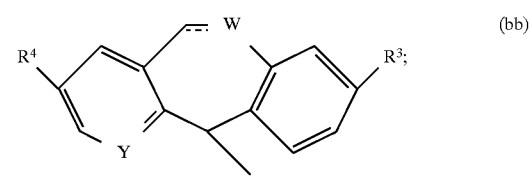

$R^6$ is selected from H or $C_1$ to $C_6$ alkyl;
$R^7$ is selected from H, $C_1$ to $C_6$ alkyl, haloalkyl, or $-C(O)R^{11}$ wherein $R^{11}$ is selected from $C_1$ to $C_6$ alkyl, $C_1$ to $C_6$ alkoxy or $-NHR^{12}$ (wherein $R^{12}$ is $C_1$ to $C_6$ alkyl or H), or R7 is an acyl radical of a naturally occurring amino acid;
$R^8$, $R^9$ and $R^{10}$ are independently selected from H, $C_1$ to $C_4$ alkyl, $C_3$ to $C_6$ cycloalkyl, heteroaryl as defined previously, heterocycloalkyl as defined previously, aralkyl, or $C_6$ to $C_{15}$ aryl; said alkyl, cycloalkyl, heteroaryl, heterocycloalkyl, aralkyl, or aryl are optionally substituted with $C_1$ to $C_4$ alkoxy, aralkyl, aryl as defined previously, heteroaryl as defined previously, cyclopropyl, heterocycloalkyl as defined previously, halogen, $-OH$, $-C(O)R^{13}$, $-SO_2R^{13}$, or $-NR^{14}R^{15}$ wherein $R^{13}$ is selected from $C_1$ to $C_4$ alkyl or aralkyl, and wherein $R^{14}$ and $R^{15}$ are independently selected from H, $C_1$ to $C_4$ alkyl or aralkyl, with the provisos that
$R^8$ may not be H in substituents (e), (f), or (k),
$R^9$ may not be H in substituents (h) or (n), and
$R^8$, $R^9$, or $R^{10}$ may not be $CH_2OH$ or $CH_2NR^{14}R^{15}$ when $R^{10}$ is directly attached to a heteroatom which is O, S, or N:
$R^{16}$ is selected from H, arylalkyl and $C_1$ to $C_6$ alkyl:
  optionally, when $R^8$ and $R^9$ are bound to the same nitrogen, $R^8$ and $R^9$, together with the nitrogen to which they are bound, form a 5 to 7 membered heterocycloalkyl ring;
  optionally, when $R^9$ and $R^{10}$ are bound to the same nitrogen, $R^9$ and $R^{10}$, together with the nitrogen to which they are bound, form a 5 to 7 membered heterocycloalkyl ring;
- - - - represents an optional bond;
W is selected from CH when the optional bond is present or $CH_2$, O, and S when the optional bond is absent;

X is selected from CH or N;
Y is N; and
Z is —NR$^{16}$—CO—.

2. The compound of claim 1 wherein R$^3$ and R$^4$ are halogen.

3. The compound of claim 2 wherein R$^3$ is Cl and R$^4$ is Br.

4. The compound of claim 1 wherein Y is N.

5. The compound of claim 1 wherein X is N.

6. The compound of claim 1 wherein R$^1$ is selected from

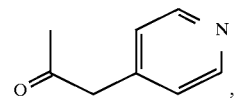 (a)

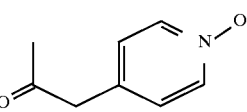 (b)

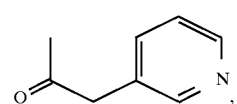 (c)

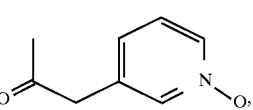 (d)

 (l)

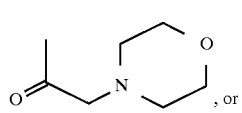 (z.1), or

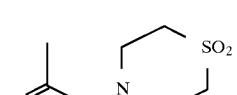 (z.2).

7. The compound of claim 1 wherein R$^1$ is selected from

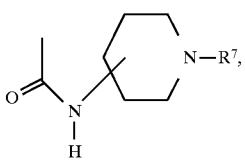 (m)

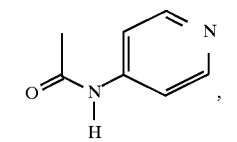 (n)

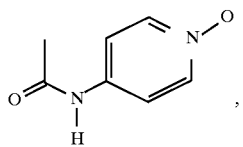 (o)

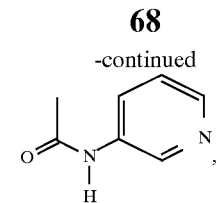 (p)

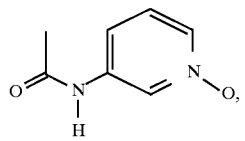 (q)

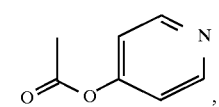 (r)

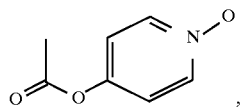 (s)

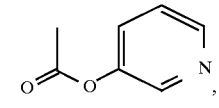 (t)

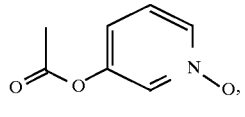 (u)

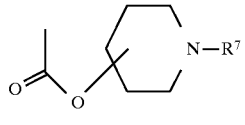 (v)

8. The compound of claim 1 wherein R$^1$ is selected from

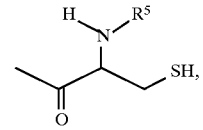 (e)

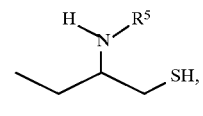 (f)

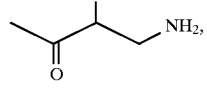 (g)

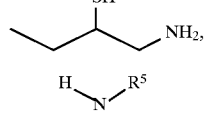 (h)

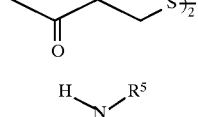 (w)

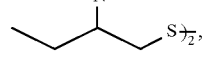 (x)

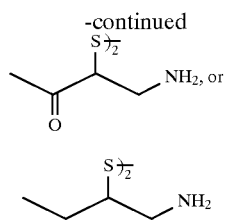

9. The compound of claim 1 wherein R¹ is

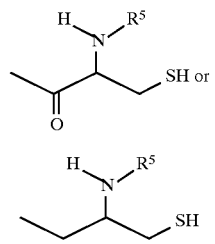

10. The compound of claim 9 wherein R⁵ is H.
11. The compound of claim 1 wherein R² is selected from H, —C₄H₉, —CH₂C₆H₅, —CH₂CH₂OCH₃, —CH₂CH₂SCH₃, —CH₂CH₂O-n-C₃H₇, —CH₂CH₂CH₂OCH₃,

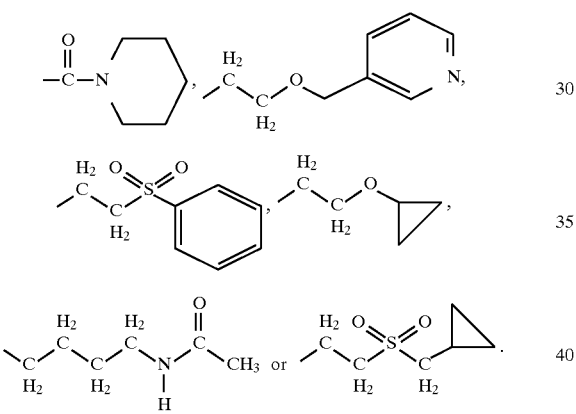

12. The compound of claim 1 wherein W is CH or CH₂, Y is N, and X is N.
13. The compound of claim 12 wherein R³ is Cl and R⁴ is Br.
14. The compound of claim 13 wherein R¹ is

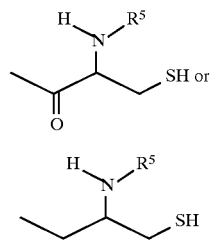

wherein R⁵ is H, and R² is selected from H, —C₄H₉, —CH₂C₆H₅, —CH₂CH₂OCH₃, —CH₂CH₂SCH₃, —CH₂CH₂O-n-C₃H₇, —CH₂CH₂CH₂OCH₃,

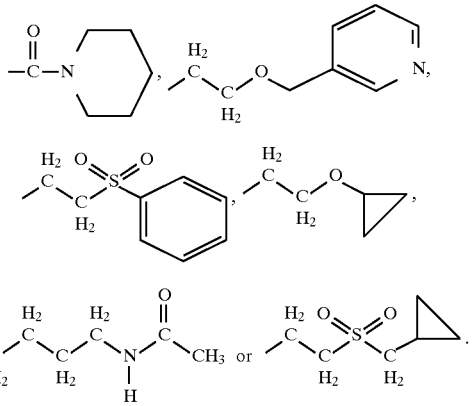

15. The compound of claim 14 having the formula:

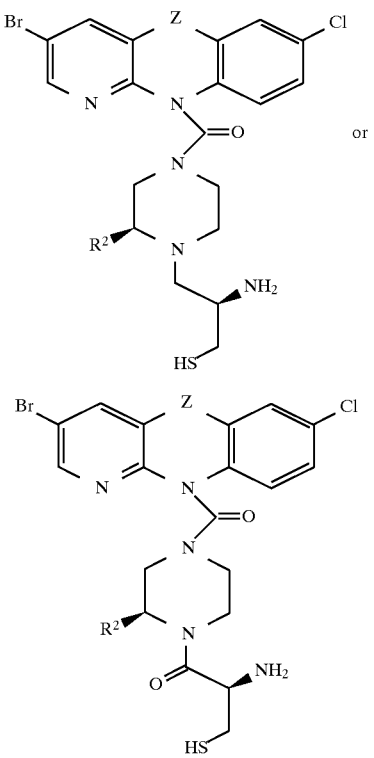

16. A pharmaceutical composition for inhibiting farnesyl protein transferase comprising an effective amount of a compound of claim 1 in combination with a pharmaceutically acceptable carrier.

17. A method for inhibiting farnesyl protein transferase in a patient in need of such treatment comprising administering an effective amount of a compound of claim 1.

* * * * *